United States Patent
Bunel et al.

(10) Patent No.: US 6,369,257 B1
(45) Date of Patent: Apr. 9, 2002

(54) HYDROFORMYLATION OF OLEFINS USING SUPPORTED BIS(PHOSPHORUS) LIGANDS

(75) Inventors: Emilio E. Bunel; Patrick Michael Burke, both of Wilmington; Joe Douglas Druliner, Newark; Leo Ernest Manzer, Wilmington; Kenneth Gene Moloy, Newark; Manxue Wang, Wilmington, all of DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/784,909

(22) Filed: Feb. 16, 2001

Related U.S. Application Data

(62) Division of application No. 09/291,878, filed on Apr. 14, 1999.
(60) Provisional application No. 60/087,151, filed on May 29, 1998.

(51) Int. Cl.⁷ ............................. C07F 17/02; C07C 45/50
(52) U.S. Cl. ............................. 556/136; 556/14; 556/40; 568/429; 568/451; 568/454
(58) Field of Search ............................. 556/14, 40, 136; 568/454, 451, 429

(56) References Cited

U.S. PATENT DOCUMENTS

| | | |
|---|---|---|
| 3,496,215 A | 2/1970 | Drinkard et al. |
| 3,631,191 A | 12/1971 | Kane et al. |
| 3,655,723 A | 4/1972 | Drinkard et al. |
| 3,766,237 A | 10/1973 | Chia et al. |
| 5,235,113 A | 8/1993 | Sato et al. |
| 5,288,918 A * | 2/1994 | Maher et al. ............... 568/454 |
| 5,432,289 A | 7/1995 | Pugin et al. |
| 5,512,695 A | 4/1996 | Kreutzer et al. |
| 5,512,696 A | 4/1996 | Kreutzer et al. |
| 5,710,344 A | 1/1998 | Breikss et al. |

FOREIGN PATENT DOCUMENTS

| | | |
|---|---|---|
| EP | 0040891 | 12/1981 |
| EP | 0864577 A2 | 9/1998 |
| EP | 0877029 A2 | 11/1998 |
| WO | WO 93/03839 | 3/1993 |
| WO | WO 95/14659 | 6/1995 |
| WO | WO 97/33854 | 9/1997 |
| WO | WO 99/06146 | 2/1999 |

OTHER PUBLICATIONS

Tolman et al. *Advances in Catalyysis*, 33, 1, 1985.
M.J. Baker et al., *J. Chem. Soc., Chem. Commun.*, 1292, 1991.
Baker et al., *J. Chem. Soc., Chem. Commun.*, 803, 1991.
Charles U. Pittman, Jr. et al., Styrene Hydroformylation Catalyzed by Homogeneous and Polymer–Anchored Rhodium Complexes. The Effect of Cis–Chelting Phosphine., *J. Org. Chem.*, 43(26), 4928–4932, 1978.
Abstract: XP–002111722 (1981).

* cited by examiner

Primary Examiner—Sreeni Padmanabhan

(57) ABSTRACT

Supported bis(phosphorus) ligands are disclosed for use in hydroformylation reactions, including the hydroformylation of olefins. Catalysts are formed when the ligands are complexed with a catalytically active metal (e.g., rhodium or iridium).

7 Claims, No Drawings

HYDROFORMYLATION OF OLEFINS USING SUPPORTED BIS(PHOSPHORUS) LIGANDS

This application is a divisional application of co-pending Ser. No. 09/291,878, filed on Apr. 14, 1999, which claims priority from provisional application No. 60/087,151, filed on May 29, 1998.

FIELD OF THE INVENTION

The invention generally relates to the hydroformylation of unsaturated organic compounds utilizing supported bis (phosphorus) ligands. In particular, the invention relates to the hydroformylation of olefins utilizing supported bis (phosphorus) ligands.

BACKGROUND OF THE INVENTION

Phosphorus ligands are ubiquitous in catalysis, finding use for a number of commercially important chemical transformations. Phosphorus ligands commonly encountered in catalysis include phosphines (A), and phosphites (B), shown below. In these representations R can be virtually any organic group. Monophosphine and monophosphite ligands are compounds which contain a single phosphorus atom which serves as a donor to a metal. Bisphosphine, bisphosphite, and bis(phosphorus) ligands in general, contain two phosphorus donor atoms and normally form cyclic chelate structures with transition metals.

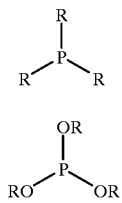

Two industrially important catalytic reactions using phosphorus ligands of particular importance are olefin hydrocyanation and olefin hydroformylation. Phosphite ligands are particularly good ligands for both of these transformations. For example, the hydrocyanation of ethylenically unsaturated compounds using transition metal complexes with monodentate phosphite ligands is well documented in the prior art. See, for example, U.S. Pat. Nos. 3,496,215, 3,631, 191, 3,655,723 and 3,766,237, and Tolman et al., *Advances in Catalysis*, 33, 1, 1985. Bidentate bisphosphite ligands have been shown to be useful in the hydrocyanation of monoolefinic and diolefinic compounds, as well as for the isomerization of non-conjugated 2-alkyl-3-monoalkenenitriles to 3- and/or 4-monoalkene linear nitrites. See, for example, U.S. Pat. Nos. 5,512,695, 5,512, 696 and WO 9514659. Bidentate phosphite ligands have also been shown to be particularly useful ligands in the hydrocyanation of activated ethylenically unsaturated compounds. See, for example, Baker, M. J., and Pringle, P. G., *J. Chem. Soc.*, Chem. Commun., 1292, 1991; Baker et al., *J. Chem. Soc.*, Chem. Commun., 803, 1991; WO 93,03839. Bidentate phosphite ligands are also useful for alkene hydroformylation reactions. For example, U.S. Pat. No. 5,235,113 describes a hydroformylation process in which an organic bidentate ligand containing two phosphorus atoms linked with an organic dihydroxyl bridging group is used in a homogeneous hydroformylation catalyst system also comprising rhodium. This patent describes a process for preparing aldehydes by hydroformylation of alkenically unsaturated organic compounds, for example 1-octene or dimerized butadiene, using the above catalyst system. Also, phosphite ligands have been disclosed with rhodium in the hydroformylation of functionalized ethylenically unsaturated compounds: Cuny et al., *J. Am. Chem. Soc.*, 1993, 115, 2066. These prior art examples demonstrate the utility of bisphosphite ligands in catalysis.

While these prior art systems represent commercially viable catalysts, they do suffer from significant drawbacks. Primarily, the catalyst, consisting of the ligand and the metal, must be separated from the reaction products. Typically this is done by removing the product and catalyst mixture from the reaction zone and performing a separation. Typical separation procedures involve extraction with an immiscible solvent, distillation, and phase separations. In all of these examples some of the catalyst, consisting of the ligand and/or the metal, is lost. For instance, distillation of a volatile product from a non-volatile catalyst results in thermal degradation of the catalyst. Similarly, extraction or phase separation results in some loss of catalyst into the product phase. These ligands and metals are often very expensive and thus it is important to keep such losses to a minimum for a commercially viable process.

One method to solve the problem of catalyst and product separation is to attach the catalyst to an insoluble support. Examples of this approach have been previously described, and general references on this subject can be found in "Supported Metal Complexes", D. Reidel Publishing, 1985, Acta Polymer. 1996, 47, 1, and Comprehensive Organometallic Chemistry, Pergamon Press, 1982, Chapter 55. Specifically, monophosphine and monophosphite ligands attached to solid supports are described in these references and also in *Macromol. Symp.* 1994, 80, 241. Bisphosphine ligands have also been attached to solid supports and used for catalysis, as described in for example U.S. Pat. No. 5,432,289, *J. Mol. Catal.* A 1996, 112, 217, and *J. Chem. Soc.*, Chem. Commun. 1996, 653. The solid support in these prior art examples can be organic, e.g., a polymer resin, or inorganic in nature.

Commonly assigned copending provisional application Ser. No. 60/054,003, filed Jul. 29, 1997, overcomes many of the problems associated with catalytic hydrocyanation by utilizing supported bis(phosphorus) ligands coordinated to nickel for hydrocyanation of olefins.

These prior art systems have to date suffered from several drawbacks and have not reached commercial potential. Among the drawbacks noted in the literature are metal leaching and poor reaction rates. In addition, the prior art systems are often not readily amenable to precise control of the ligand coordination properties, e.g., electronics and steric size. What is needed is a supported bis(phosphorus) ligand system which overcomes the problems and deficiencies inherent in the prior art with respect to hydroformlyation. Other objects and advantages of the present invention will become apparent to those skilled in the art upon reference to the detailed description which hereinafter follows.

SUMMARY OF THE INVENTION

The present invention provides for the hydroformylation of olefins utilizing supported diols and chelating bis (phosphorus) ligands covalently bonded to a support. Preferably, the support is an insoluble polymer such as a crosslinked polystyrene resin or other organic polymer resin.

The supported bis(phosphorus) ligand has the structure (2):

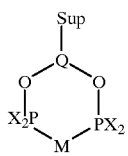

(2)

wherein:
- Q is any organic fragment which binds a $OPX_2$ moiety to the support (Sup); and
- X is an alkoxy, aryloxy, alkyl, or aryl.

Preferably, X is aryloxide or aryl.

The supported catalyst composition has the structure (3):

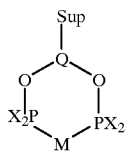

(3)

wherein:
- Q is any organic fragment which binds a $OPX_2$ moiety to the support (Sup);
- X is an alkoxy, aryloxy, alkyl or aryl; and
- M is a transition metal capable of carrying out catalytic transformations.

X is preferably aryloxide or aryl and M is preferably Ni, Rh, Co, Ir, Pd, Pt or Ru.

In particular, the invention provides for a hydroformylation process comprising reacting an acyclic, monoethylenically unsaturated compound with CO and $H_2$ in the presence of a supported catalyst composition according to formula (3):

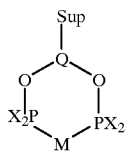

(3)

wherein:
- Q is any organic fragment which binds a $OPX_2$ moiety to the support (Sup);
- X is an alkoxy, aryloxy, alkyl or aryl; and
- M is selected from the group consisting of rhodium and iridium The invention further provides for the hydroformylation of aromatic olefins comprising reacting an acyclic aromatic olefin compound with CO and $H_2$ in the presence of a supported catalyst composition according to formula (3):

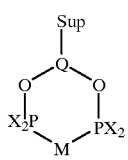

(3)

wherein:
- Q is any organic fragment which binds a $OPX_2$ moiety to the support (Sup);
- X is an alkoxy, aryloxy, alkyl or aryl; and
- M is rhodium.

This process may be run in either the liquid or vapor phase.

Also disclosed is a process for the preparation of a supported rhodium bisphosphite hydroformylation catalyst comprising reacting CO and $H_2$ with a rhodium compound in the presence of a supported bis(phosphorus) ligand of formula 1

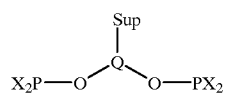

1 in which Q is any organic fragment which binds the two phosphorus moieties to the support and X is alkoxy, aryloxy, alkyl, or aryl, or alternatively wherein the $PX_2$ moiety forms a ring and $X_2$ is a di(alkoxy), di(aryloxy), di(alkyl), or di(aryl). In a preferred embodiment, the supported ligand of Formula (1) is further characterized according to Formula (4)

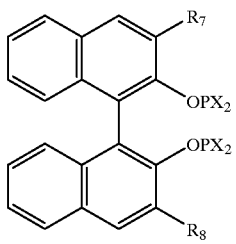

4 wherein:
- the linker Q is a 2,2'-dihydroxyl-1,1'-binaphthalene bridging group;
- the substituents $R_7$ and $R_8$ in the 3,3' positions of the binaphthalene bridging group are selected from alkyl group containing 2 to 10 carbon atoms, an aryl group, an alkoxy group, an aryloxy group, a carboalkoxy group, a carboaryloxy group, a nitrile group, a triarylsilyl group, or trialkylsilyl group;
- at least one of the groups $R_7$ and $R_8$ are covalently attached to a support (Sup);
- X is an alkoxy, aryloxy, alkyl, or aryl, or alternatively the $PX_2$ moiety forms a ring and $X_2$ is a di(alkoxy), di(aryloxy), di(alkyl), or di(aryl).

DETAILED DESCRIPTION OF THE PREFERRED EMBODIMENTS

A primary aim of this invention is to provide an improved hydroformylation reaction utilizing the catalysts covalently attached to an insoluble support, described in copending commonly assigned provisional application Ser. No. 60/054,003, filed Jul. 29, 1997. The advantages of this process are:

These catalysts are insoluble and non-volatile, allowing ready separation from the reaction medium by filtration or other means, or use in fixed bed, flow-through reactors using either liquid or gas phase carrier streams.

The chelating arrangement of donor atoms gives catalysts with commercially practical activity and selectivity. In particular, the chelates described herein are based on bisphosphite ligands, in which it is known that soluble derivatives give catalysts with significantly improved reaction rates and selectivities over monophosphite ligands.

The chelating arrangement of donor atoms results in a much stronger ligand-metal interaction and thus greatly minimizes the potential for metal leaching.

It is possible to methodically alter the spacing between the chelating atoms, the steric environment of these atoms, and the electronic properties of the donor atoms, thereby offering precise control of ligand coordination properties; this in turn allows significant opportunity to optimize catalyst performance.

The chemical environment in the immediate vicinity of the catalytically active site is uniform throughout the solid support matrix. The catalyst therefore acts as a "single site" type of catalyst, as opposed to an ensemble of different catalysts.

The supported bis(phosphorus) ligands described herein generally form the catalyst when combined with a catalytically active metal. The resulting supported catalyst forms a separate phase from the reaction medium, reacting substrates, and products. The reaction medium may be composed of a liquid solvent which does not interfere with the catalytic reaction of interest, or may be gaseous, e.g., an inert carrier gas and gaseous reactants and products.

Description of the Support

Virtually any solid material may be used as a support in the context of this invention as long as it meets the following criteria:

The material is insoluble in organic, aqueous, or inorganic solvents. Organic polymer supports are acceptable in this regard but they generally need to be crosslinked. Inorganic supports, such as metal oxides (silicas, etc.) are generally insoluble in these solvents and also may be used as supports.

The support contains reactive sites which can be used for the covalent attachment of organic fragments containing a diol group (as described below) or a protected diol group.

The reactive sites are isolated to prevent additional crosslinking during further chemical transformations.

The reactive sites are exposed to the reaction medium. With a polymer resin support this is achieved through the use of resins which swell in a reaction solvent or is sufficiently porous to allow transport of the reaction medium through the polymer matrix.

The term "solid support" or "support" (sup) refers to a material having a rigid or semi-rigid surface which contain or can be derivatized to contain functionality which covalently links a compound to the surface thereof. Such materials are well known in the art and include, by way of example, polystyrene supports, polyacrylamide supports, polyethyleneglycol supports, metal oxides such as silica, and the like. Such supports will preferably take the form of small beads, pellets, disks, or other conventional forms, although other forms may be used.

The supports described in this application are functionalized poly(styrene) resins. Other suitable polymers include polyolefins, polyacrylates, polymethacrylates, and copolymers thereof that meet the general criteria described above. Specifically, poly(styrene) resins commonly used for solid phase synthesis have been used. These particular resins are crosslinked with from I to 10 wt % divinylbenzene. The styrene moieties are substituted in the para or meta positions. Only a portion of the styrene moieties are substituted, typically resulting in functional group loadings of approximately 0.2 to 2.0 mmole per gram of resin, although this value may be higher or lower.

Description and Preparation of Supported Diols

The aims of this invention are achieved by construction of a chelating ligand covalently bonded to an insoluble support (Sup), preferably a polymer support (Pol). The first step of this procedure involves the preparation of a diol group covalently attached to an insoluble support as exemplified by the following structure:

(1)

wherein, Sup represents the insoluble support. As used herein, Q means any organic fragment which binds the diol moiety to the support. For example, Q may consist of from 2 to 50 carbon atoms, in addition to heteroatoms such as nitrogen, oxygen, and the like. Q may additionally contain functional groups such as ether, acetal, ketal, ester, amide, amine, imine, etc., and combinations thereof. Q may also contain saturated or unsaturated carbon-carbon bonds. Q may or may not be symmetrical.

The number of atoms present in Q and used to separate the two OH moieties of the diol is generally limited to between 2 and 10, although any number and arrangement which ultimately allows the formation of a chelating ring is acceptable. A preferred number is 2 to 5 atoms. These atoms may be carbon or heteratoms such as oxygen and nitrogen. The atoms may further comprise a chain or cyclic structure, the latter of which may be saturated or unsaturated, e.g., aromatic.

The preparation of materials of Formula 1 follows methods known to those skilled in the art. The procedure may involve one reaction step or multiple reaction steps. Preferred methods are those which proceed in high yield, high selectivity, are inexpensive, and are simple to conduct. For example, *Can. J. Chem.* 1973, 51, 3756, describes the synthesis of the material of formula SD6. The synthesis occurs in two reaction steps from inexpensive materials and in high yield. Other materials described in this invention have not been previously reported in the literature but follow reaction steps known for soluble, non-polymer supported analogues. For instance, reaction of the polymer-supported benzaldehyde pol-CHO, prepared by the method described in *J. Polym. Sci.*1975, 13, 1951 and *J. Polym. Sci., Polym. Lett.* 1965, 3, 505, with pentaerythritol gives polymer-supported diol SD1. The analogous reaction of soluble, non-polymer supported benzaldehyde with pentaerythritol is described in *Org. Syn.* Vol 38, 65. Alternatively, reaction of polymer-supported aldehyde pol-CHO with diethyl tartrate, followed by reduction, leads to the class of polymer-supported diols SD2, 3, 4. SD3 is described in *J. Org. Chem.,* 1997, 62, 3126. The analogous reactions of the soluble, non-polymer supported compounds are described in *Helv. Chim. Acta* 1983, 66, 2308 and *J. Org. Chem.* 1993, 58, 6182. Supported alkylene-bridged bisaryl alcohols can be prepared by methods found in *J. Chem. Soc., Perkin I,* 1980, 1978–1985; *Indian J. Chem.* 1995, 34B, 6–11, and *Chem. Ber.* 1985,118, 3588–3619. Other examples may be prepared by known organic transformations, and representative structures are shown below.

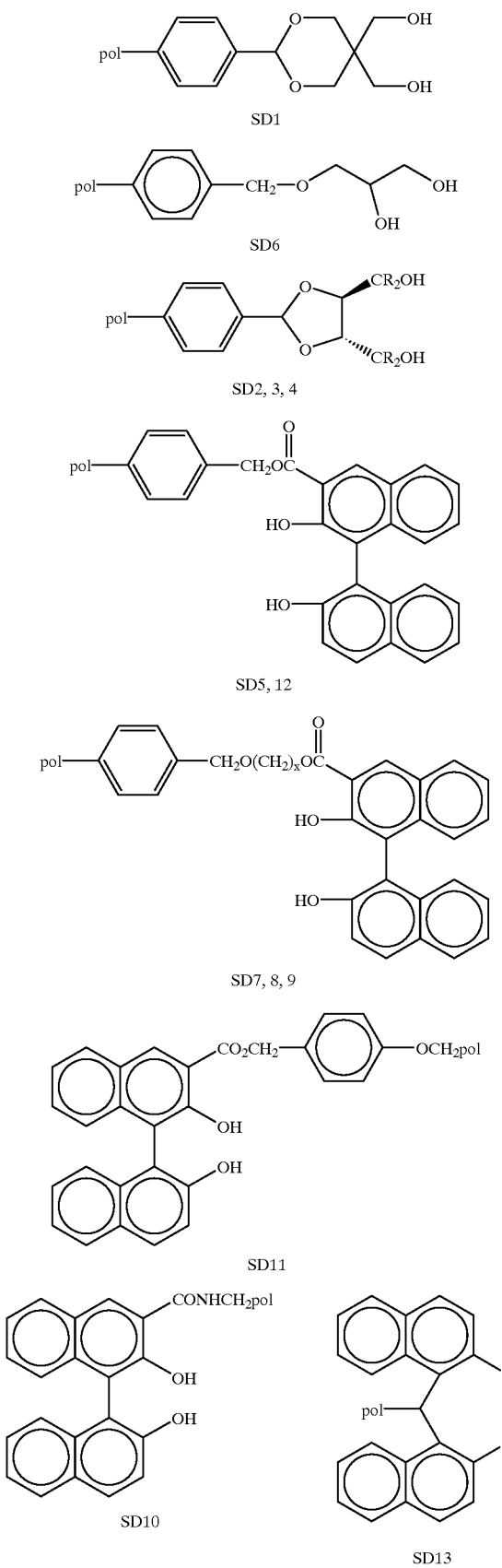

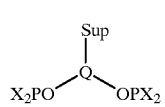

Description and Preparation of Polymer-Supported Bis(Phosphorus)Ligands

The polymer-supported bis(phosphorus) ligands may be prepared by a variety of methods known in the art, for example, see descriptions in WO 93,03839; U.S. Pat. Nos. 4,769,498 and 4,668,651. In general, the transformation involves the reaction of a phosphorus halide, typically but not limited to chloride, with the diol to form P-O bonds. The phosphorus halide may be any compound of the type $PY_nX_{3-n}$, where Y=halide, X=alkoxide, aryloxide, alkyl, aryl, and n=3, 2, or 1. The phosphorus halides most useful for the present invention are those where Y=Cl; X=alkoxide, aryloxide, alkyl, or aryl; and n=1. The group X may contain from 1 to 50 carbon atoms. It may also optionally contain heteroatoms such as oxygen, nitrogen, halogen, and the like, and also functional groups such as ethers, alcohols, esters, amides, as well as others. The groups X may or may not be linked to form a cyclic structure. The $PX_2$ moiety may form a ring and $X_2$ may be a di(alkoxide), di(aryloxide), di(alkyl) or di(aryl). Many dialkylchlorophosphines and diarylchlorophosphines are commercially available, or may be prepared by methods known in the art, for example, *J. Am. Chem. Soc.* 1994, 116, 9869. Phosphorochloridites, may be prepared by a variety of methods known in the art, for example, see descriptions in *Polymer* 1992, 33, 161; *Inorg. Syn.* 1966, 8, 68; U.S. Pat. No. 5,210,260; *Z. Anorg. Allg. Chem.* 1986, 535, 221. For example, the reaction of 2,2'-biphenol with phosphorus trichloride gives 1,1'-biphenyl-2,2'-diylphosphorochloridite.

The reaction of these chlorophosphorus reagents with a material of Formula 1 in the presence of a base gives a polymer-supported bis(phosphorus) ligand exemplified by the structure shown:

(2)

$$\underset{X_2PO}{\overset{\overset{\displaystyle Sup}{|}}{\phantom{X}}}\overset{Q}{\diagdown}OPX_2$$

where X and Q are as defined above. Other examples may be prepared by similar transformations, and representative structures are also shown below.

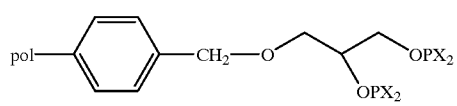

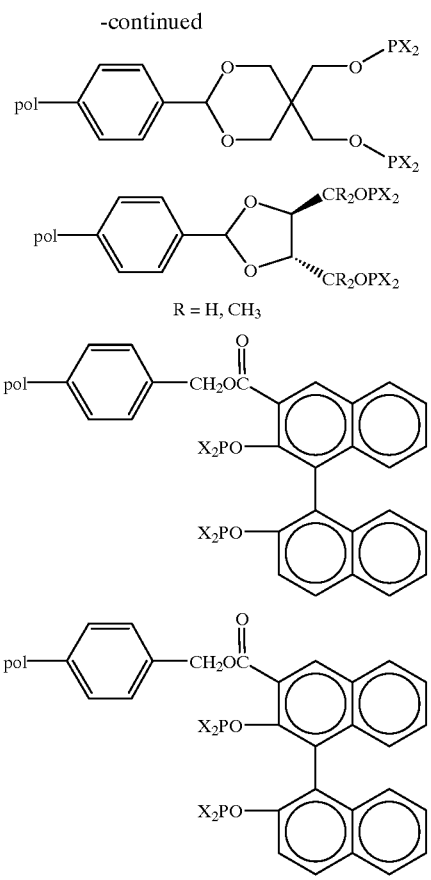

R = H, CH₃

Description and Preparation of Polymer-Supported Transition Metal Catalysts

The transition metal catalysts which are a subject of this invention are defined by the formula shown below:

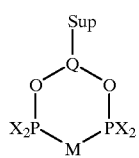

(3)

wherein Q and X are as defined above. M is a transition metal capable of carrying out catalytic transformations. M may additionally contain labile ligands which are either displaced during the catalytic reaction, or take an active part in the catalytic transformation. Any of the transition metals may be considered in this regard. The preferred metals are those comprising groups 8, 9, and 10 of the Periodic Table. The preferred metals for hydroformylation are rhodium, cobalt, iridium, palladium and platinum, the most preferred being rhodium.

The zero-valent rhodium compounds, suitable for hydroformylation, can be prepared or generated according to techniques well known in the art, as described, for example, WO 95 30680, U.S. Pat. No. 3,907,847, and J. Amer. Chem. Soc., 115, 2066, 1993. Zero-valent rhodium compounds that contain ligands which can be displaced by the organophosporus ligands are a preferred source of zero-valent rhodium. Examples of such preferred zero-valent rhodium compounds are $Rh(CO)_2$ (acetylacetonate) and $Rh(CO)_2$ $(C_4H_9COCHCO\text{-}t\text{-}C_4H_9)$, $Rh_2O_3$, $Rh_4(CO)_{12}$, $Rh_6(CO)_{16}$, $Rh(O_2CCH_3)_2$, and Rh(2-ethylhexanoate). Rhodium supported on carbon may also be used in this respect.

Description of Catalytic Processed-Hydroformylation of Monoolefinic Compounds The present invention also provides a process for hydroformylation, comprising reacting an acyclic, monoethylenically unsaturated compound with a source of CO and $H_2$ in the presence of a catalyst composition formed by the supported rhodium catalysts described previously and depicted by Formula 3.

Representative ethylenically unsaturated compounds which are useful in the process of this invention are shown in Formula I, III or V, and the corresponding terminal aldehyde compounds produced are illustrated by Formula II, IV or VI, respectively, wherein like reference characters have same meaning.

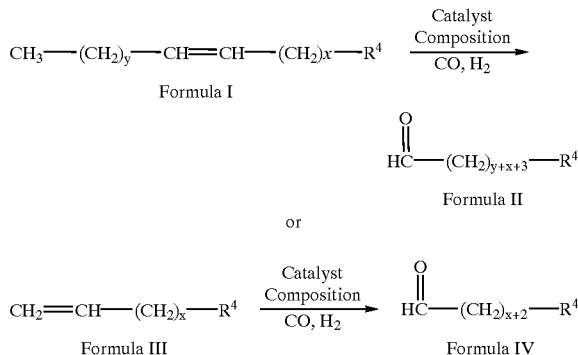

wherein
$R^4$ is H, CN, $CO_2R^5$, or perfluoroalkyl;
y is an integer of 0 to 12;
x is an integer of 0 to 12 when $R^4$ is H, $CO_2R^5$ or perfluoroalkyl;
x is an integer of 1 to 12 when $R^4$ is CN; and
$R^5$ is alkyl.

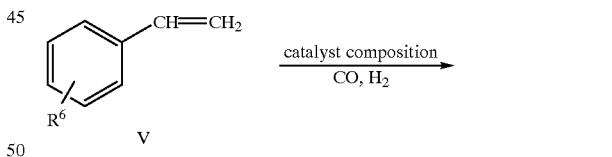

$R^6$ is an alkyl, aryl, aralkyl, alkaryl, or fused aromatic group of up to 20 carbon atoms; $R^6$ may further be branched or linear; $R^6$ may also contain heteroatoms such as O, N, and F.

The nonconjugated acyclic, aliphatic, monoolefinically unsaturated starting materials useful in this invention include unsaturated organic compounds containing from 2 to approximately 30 carbon atoms. The monoolefins propylene, 1-butene, 2-butene, methyl 3-pentenoate, methyl 4-pentenoate, 3-pentenenitrile, and 4-pentenenitrile are especially preferred. As a practical matter, when the nonconjugated acyclic aliphatic monoethylenically unsaturated compounds are used in accordance with this invention, up to about 10% by weight of the monoethylenically unsaturated compound may be present in the form of a conjugated isomer, which itself may undergo hydroformylation. As used herein, the term "pentenenitrile" is intended to be identical with "cyanobutene". Suitable unsaturated compounds include unsubstituted hydrocarbons as well as hydrocarbons substituted with groups which do not attack the catalyst, such as cyano. These unsaturated compounds include monoethylenically unsaturated compounds containing from 2 to 30 carbons such as ethylene, propylene, butene-1, pentene-2, hexene-2, etc.; nonconjugated diethylenically unsaturated compounds such as allene; and substituted compounds such as 3-pentenenitrile, 4-pentenenitrile, methyl pent-3-enoate; and ethylenically unsaturated compounds having perfluoroalkyl substituents such as, for example, $C_zF_{2z+1}$, where z is an integer of up to 20. The monoethylenically unsaturated compounds may also be conjugated to an ester group such as methyl pent-2-enoate.

Preferred are nonconjugated linear alkenes, nonconjugated linear alkenenitriles, nonconjugated linear alkenoates, linear alk-2-enoates and perfluoroalkyl ethylenes. Most preferred substrates include 3- and 4-pentenenitrile, alkyl 2-, 3-, and 4-pentenoates, and $C_zF_{2z+1}CH=CH_2$ (where z is 1 to 12).

The preferred products are terminal alkanealdehydes, linear dialdehyde alkylenes, linear aliphatic aldehyde esters, and 3-(perfluoroalkyl)propioaldehyde. Most preferred products are n-butyraldehyde, methyl 5-formylvalerate, 2-phenyl-propionaldehyde, and 5-cyanovaleraldehyde.

The reaction conditions of the hydroformylation process according to this invention are in general the same as used in a conventional process, described, for example, in U.S. Pat. No. 4,769,498, which is incorporated herein by reference and will be dependent on the particular starting ethylenically unsaturated organic compound. For example, the temperature can be from room temperature to 200° C., preferably from 50–120° C. The pressure may vary from atmospheric pressure to 20 MPa, preferably from 0.15 to 10 MPa and more preferably from 0.2 to 1 MPa. The pressure is, as a rule, equal to the combined hydrogen and carbon monoxide partial pressure. Extra inert gases may however be present. The molar ratio of hydrogen to carbon monoxide is generally between 10 to 1 and 1 to 10, preferably between 6 to 1 and 1 to 2.

The amount of rhodium compound is not specially limited, but is optionally selected so that favorable results can be obtained with respect to catalyst activity and economy. In general, the concentration of rhodium in the reaction medium is between 10 and 10,000 ppm and more preferably between 50–500 ppm, calculated as the free metal.

The molar ratio of multidentate phosphorus ligand to rhodium is not specially limited, but is optionally selected so that favorable results can be obtained with respect to catalyst activity and aldehyde selectivity. This ratio generally is from about 0.5 to 100 and preferably from 1 to 10 (moles of ligand to moles of metal).

The choice of solvent is not critical provided the solvent is not detrimental to catalyst, reactant and product. The solvent may be a mixture of reactants, such as the starting unsaturated compound, the aldehyde product and/or by-products. Suitable solvents include saturated hydrocarbons such as kerosene, mineral oil or cyclohexane, ethers such as diphenyl ether tetrahydrofuran or a polyglycol, ketones such as methyl ethyl ketone and cyclohexanone, nitrites such as methylglutaronitrile and benzonitrile, aromatics such as toluene, benzene and xylene, esters such as methyl valerate and caprolactone, dimethylformamide, and sulfones such as tetramethylenesulfone. The reaction may also be conducted with reactants and products in the gas phase.

Preferably, when a liquid reaction medium is used, the reaction mixture is agitated, such as by stirring or shaking.

For the vapor phase hydroformylation, the preferred temperature range is from about 50° C. to about 180° C., most preferably from 80° C. to 130° C. The temperature must be chosen so as to maintain all of the reactants and products in the vapor phase, but low enough to prevent deterioration of the catalyst. The particular preferred temperature depends somewhat on the catalyst being used, the olefinic compound being reacted and the desired reaction rate. The operating pressure is not particularly critical and can conveniently be from about 101.3 to 1013 kPa. The pressure and temperature combination must be chosen so that all reactants and products remain in the vapor phase.

The supported rhodium catalysts of Formula 3 are typically loaded into tubular reactors, and a gaseous olefinic compound, e.g., propylene, CO, and $H_2$ is passed continuously over the solid catalysts at temperatures sufficiently high to maintain the starting materials as well as the reaction products in the vapor phase.

Carbon monoxide, $H_2$ and/or the olefinic starting materials can be delivered as a neat vapor or as a preheated solution in a solvent, such as acetonitrile or toluene. Under atmospheric pressure, using nitrogen or other inert gas as carrier. Nitrogen is preferred because of its low cost. The reaction products are liquid at room temperature and are conveniently recovered by cooling.

EXAMPLES

The following non-limiting examples further illustrate the invention. All percentages are by weight, unless otherwise noted.

EXAMPLE 1

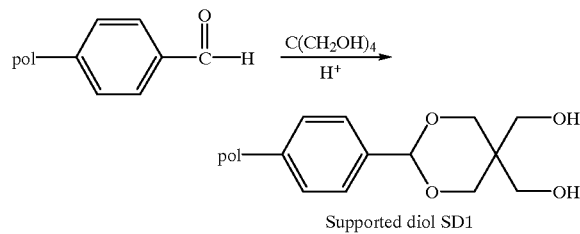

Supported diol SD1

10.2 g of pentaerythritol was dissolved in the minimum amount of dimethyl sulfoxide, and then toluene was added until the solution became slightly cloudy. 18.9 g of the polymer-supported benzaldehyde resin (prepared by oxidation of Merrifield's resin commercially available from Aldrich Chemical Co., Milwaukee, Wis., or Polymer Laboratories, Ltd., Shropshire, England) and a few crystals of p-toluenesulfonic acid were then added. The suspension was brought to reflux and the condensate was passed through a bed of molecular sieves in a Soxhlet extractor before returning to the reaction flask. After 12 h the suspension was cooled to room temperature and the resin was isolated by filtration. After washing with warm 0.5% aq $NaHCO_3$, MeOH, and then hexane the resin was dried under vacuum.

IR: O—H at 3400 cm$^{-1}$; complete loss of C=O at 1701 cm$^{-1}$.

MAS $^{13}$C{$^1$H} NMR (CDCl$_3$): δ102.7 (acetal carbon); 70.7 (ring OCH$_2$); 65.3, 63.7 (axial, equatorial CH$_2$OH); 39.6 (quaternary carbon), in addition to polymer backbone and ring resonances.

EXAMPLE 2

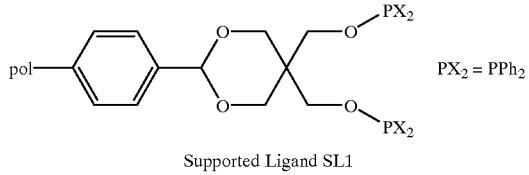

Supported Ligand SL1

1.0 g of resin-supported diol SD1 was suspended in 15 mL pyridine. 0.97 g PPh$_2$Cl was added dropwise with stirring. After 2.5 days the resin was filtered, washed with 5×10 mL pentane and then dried under vacuum.

MAS $^{13}$C{$^1$H} NMR (CDCl$_3$): δ102.7 (acetal carbon); 70.3 (ring OCH$_2$); 70.0, 68.3 (axial, equatorial CH$_2$OP), in addition to polymer backbone and ring resonances.

MAS $^{31}$P{$^1$H} NMR (CDCl$_3$): 114, 116 ppm.

EXAMPLE 3

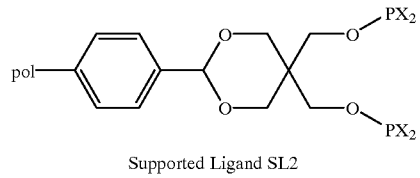

Supported Ligand SL2

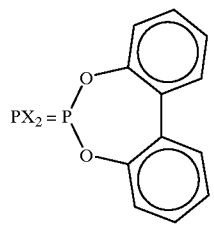

In a manner similar to Example 2, 2.0 g of SD1 was suspended in 15 mL pyridine. 4.4 g of 1,1'-biphenyl-2,2'-diylphosphorochloridite (50 wt % solution in toluene) was added dropwise. The resulting slurry was stirred overnight. The resin was filtered, washed with 2×15 mL of 50/50% CH$_2$Cl$_2$/pentane, then 3×15 mL pentane, and then dried under vacuum.

EXAMPLE 4

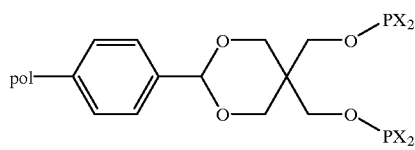

Supported Ligand SL3-1

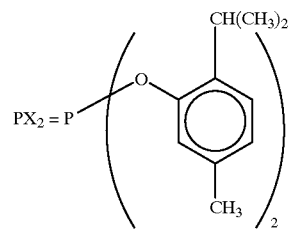

In a manner similar to Example 2, 2.0 g of SD1 was suspended in 15 mL pyridine, and 44 mL of a 0.2 M solution of bis(2-isopropyl-5-methylphenyl)phosphorochloridite in toluene was added dropwise. After stirring overnight the resin was filtered, washed with 3×10 mL 50/50 pyridine/pentane, then 2×10 mL pentane, and finally dried under vacuum.

An identical experiment was performed using a 2% divinylbenzene cross-linked resin support to give supported ligand SL3-2.

$^{31}$P{1H} (CDCl$_3$): 134 ppm.

EXAMPLE 5

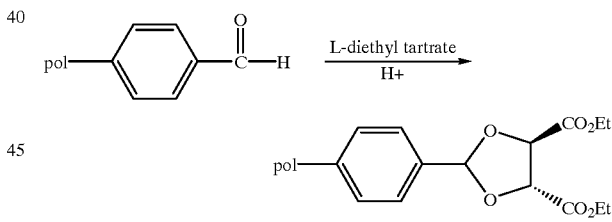

8.0 g of polymer-supported benzaldehyde resin (1% divinylbenzene cross-linked), 3.3 g diethyltartrate, and a few crystals of p-toluenesulfonic acid were combined in 50 mL toluene. The mixture was refluxed for 18 h, with the condensed vapors passing through a bed of molecular sieves before returning to the reaction flask. The resin was collected by filtration, washed with acetone (4×15 mL), CH$_2$Cl$_2$ (4×15 mL), hexane (2×15 mL), and CH$_2$Cl$_2$ before vacuum drying.

IR: —CO$_2$Et at 1730 cm$^{-1}$; complete loss of aldehyde C=O at 1701 cm$^{-1}$.

An identical experiment was conducted using 2% cross-linked resin to give a derivatized resin with an identical infrared spectrum.

EXAMPLE 6

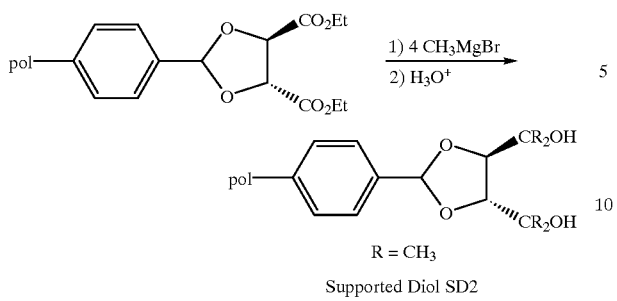

Supported Diol SD2

7.3 g polymer-supported diester of Example 5 was suspended in 100 mL dry THF and then cooled to 0° C. 11.4 mL of a 3.0 M solution of $CH_3MgBr$ in diethyl ether was added dropwise. The mixture was warmed to room temperature and then heated to 60° C. After 3.5 h the mixture was cooled to 0° C. and then quenched with aqueous HCl. The product was collected by filtration, washed with $H_2O$(3×15 mL), acetone (3×15 mL), and diethyl ether (2×15 mL), and finally vacuum dried.

IR: O—H at 3400 cm$^{-1}$; complete loss of the ester band at 1730 cm$^{-1}$.

An identical experiment was conducted using 2% cross-linked resin to give a derivatized resin with an identical infrared spectrum.

EXAMPLE 7

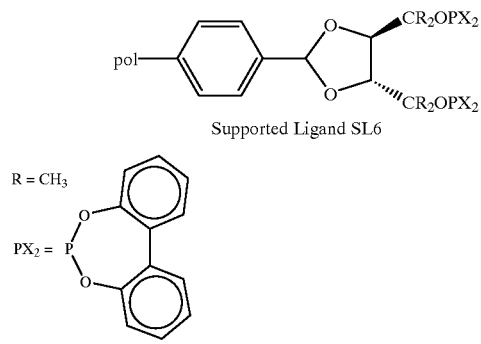

Supported Ligand SL6

5.374 g of supported diol SD2 was suspended in 50 mL toluene and 15 mL pyridine. 8.04 g 1,1'-biphenyl-2,2'-diylphosphorochloridite (50 wt % soln in toluene) was added dropwise. The mixture was heated overnight at 60° C. The product was filtered, washed with pyridine (2×15 mL), diethyl ether (3×15 mL), and hexane (15 mL) before vacuum drying.

IR: complete loss of O—H at 3400 cm$^{-1}$.

$^{31}$P NMR(CDCl$_3$): 153 ppm.

EXAMPLE 8

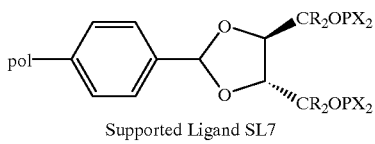

Supported Ligand SL7

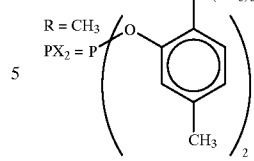

Resin-supported diol SD2 (5.0 g) was suspended in a pyridine/toluene (3/1) mixture. 3.82 g bis(2-isopropyl-5-methylphenyl)phosphorochloridite was then added dropwise with stirring at room temperature. After several hours the resin was filtered and washed with pyridine (4×25 mL), diethyl ether (2×25 mL), and pentane (2×25 mL) before vacuum drying.

IR: complete loss of O—H band.

EXAMPLE 9

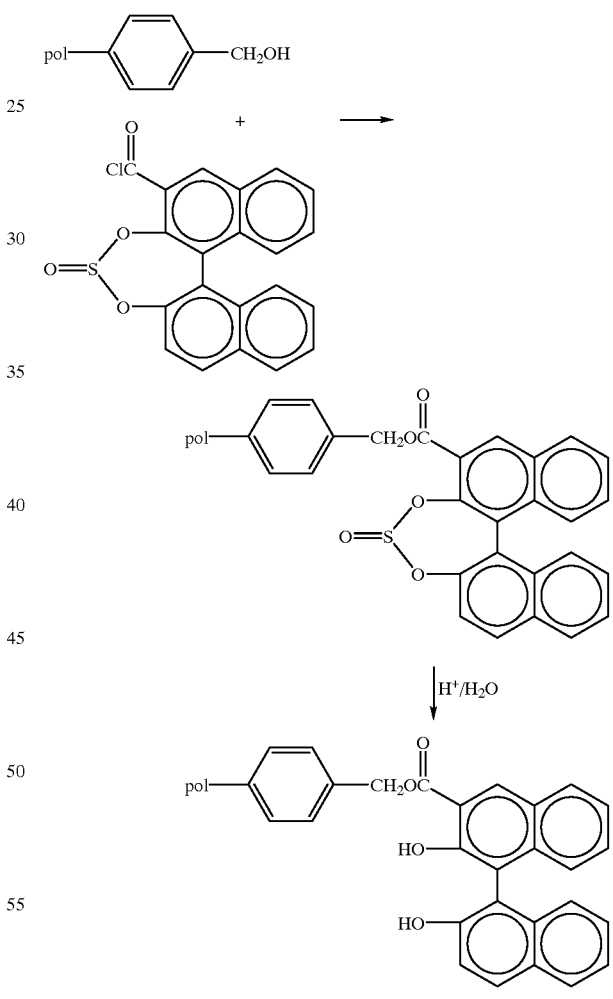

Supported Diol SD5

0.525 g of the resin-supported benzyl alcohol was suspended in 15 mL THF and then treated with 0.236 g of the sulfoxyl-protected binaphthol acid chloride shown. The sulfoxyl-protected binaphthol acid chloride was prepared by oxidative coupling of 2-naphthol with 2-hydroxy-3-naphthoic acid followed by treatment with thionyl chloride.

These transformations are well known to those skilled in the art. The mixture was stirred for 1 day at room temperature and then one day at 45° C. The reaction was quenched with H$_2$O/methanol, filtered, and the resin washed with toluene, acetone, methanol, water, acetone, and hexane before vacuum drying.

IR: O—H at 3430 cm$^{-1}$, ester C=O at 1729 cm$^{-1}$.

EXAMPLE 10

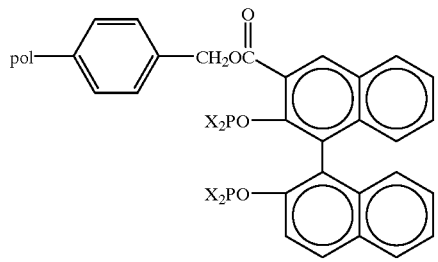

Supported Ligand SL12

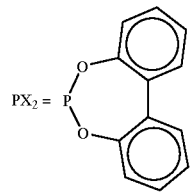

The resin-supported diol SD5 (1.80 g) was suspended in 15 mL of THF along with 1 mL of pyridine and 2.70 g of 1,1'-biphenyl-2,2'-diylphosphorochloridite (50 wt % solution in toluene). The mixture was stirred overnight at 50° C. before filtration. The product was washed with CH$_2$Cl$_2$ (3×5 mL), THF (3×5 mL), toluene (3×5 mL), and pentane (2×5 mL), before vacuum drying.

IR showed nearly complete loss of O—H at ca. 3400 cm$^{-1}$.

$^{31}$P{$^1$H} MAS NMR (CDCl$_3$): broad resonances at δ144.2 and 137.8, in addition to an unidentified component at δ12.8.

EXAMPLE 11

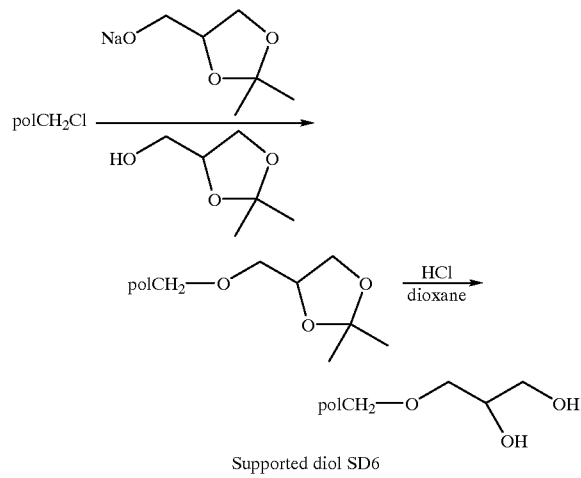

Supported diol SD6

This supported diol was prepared by the literature procedure in Can. J. Chem., 1973, 51, 3756. 18.8 g of Merrifield resin was suspended in 50 mL of solketal containing 4.70 g of the sodium salt of solketal. The mixture was stirred overnight at 80° C. The intermediate ketal was collected by filtration, and then washed with water (3×20 mL), acetone (3×20 mL), and hexane (3×20 mL).

IR (KBr): C—O—C at 1151, 1211, 1249 cm$^{-1}$.

$^{13}$C{$^1$H} MAS NMR (CDCl$_3$): δ110.1, 75.5, 74.6, 71.6, 67.7.

The supported ketal was deprotected by suspension in 200 mL of dioxane containing a small amount of 10% aq HCl. The mixture was stirred overnight at room temperature. Workup was accomplished by filtration and then washing with water, acetone, and THF before vacuum drying.

IR: (KBr): Loss of): C—O—C at 1156–1249 cm$^{-1}$; formation of O—H at 3430 cm$^{-1}$.

$^{13}$C{$^1$H} MAS NMR (CDCl$_3$): δ74.2, 72.2, 71.6, 64.8, in addition to polymer resonances.

EXAMPLE 12

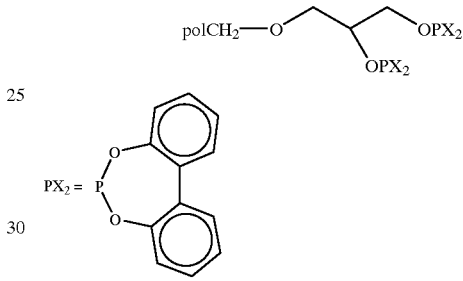

Supported Ligand SL14

1.185 g of the supported diol resin SD6 was suspended in 15 mL of THF. 1.8 g of 1,1'-biphenyl-2,2'-diylphosphorochloridite (50 wt % solution in toluene) was added dropwise, followed by 1.0 mL of pyridine. The resulting mixture was stirred at room temperature for 3 days. The product was isolated by filtration and then washed with successive portions of CH$_3$CN, CH$_2$Cl$_2$, and pentane. The product was then vacuum dried.

IR (KBr): disappearance of O—H at 3430 cm$^{-1}$.

$^{31}$P{$^1$H} MAS NMR (CDCl$_3$): δ144.4, 138.3, in addition to minor components between δ25–7.

EXAMPLE 13

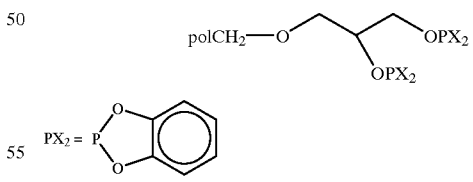

Supported Ligand SL15

1.40 g of the resin-supported diol SD6 was suspended in 15 mL of THF and then treated with 0.75 g 1,2-phenylenephosphorochloridite and 1 mL of pyridine. The resulting mixture was stirred for three days at room temperature. The product was filtered, washed with CH$_2$Cl$_2$, toluene, and pentane, and then dried under vacuum.

IR (KBr): disappearance of O—H at 3430 cm$^{-1}$.

$^{31}$P{$^1$H} MAS NMR (CDCl$_3$): δ144.2, 138.2.

EXAMPLE 14

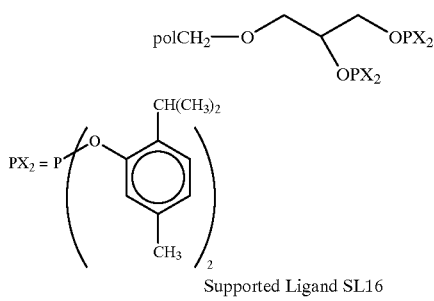

Supported Ligand SL16

1.40 g of supported diol resin SD6 was suspended in 15 mL of THF and then treated with 1.53 g of bis(2-isopropyl-5-methylphenyl)phosphorochloridite (as a toluene solution) and 1 mL of pyridine. The mixture was stirred for 3 days at room temperature. The product was filtered, washed with $CH_2Cl_2$, $CH_3CN$, and pentane before vacuum drying.

IR (KBr): disappearance of O—H at 3430 $cm^{-1}$.

$^{31}P\{^1H\}$ MAS NMR ($CDCl_3$): δ131.0, 128.6, in addition to several minor components in the ranges δ134–127 and δ25–0.

Elemental analysis: 81.44% C, 7.83% H, 3.09% P.

EXAMPLE 15

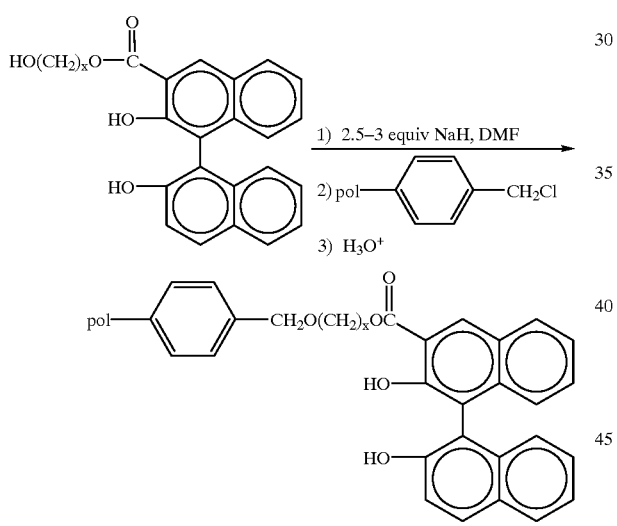

Example 15-1 x=3, Supported Diol SD7

2.33 g of the binaphthol ester shown (x=3) was dissolved in DMF. 0.39 g (2.7 equiv) of NaH was added to give gas evolution and an orange solution. After 20 min at room temperature the solution was treated with 4.0 g of Merrifield's resin (4.8 mmol $CH_2Cl$). The mixture was stirred overnight at 98° C. The resulting resin was isolated by filtration and then washed with 95% EtOH, acetone, THF, toluene, and hexane before drying under vacuum.

IR (KBr, $cm^{-1}$): 3441 and 3223 (O—H), 1685 (C=O).

Example 15-2 x=4, Supported Diol SD8

In a similar manner, 5.83 g of the binaphthol monoester (x=4), 0.94 g NaH, and 9.6 g of Merrifield's resin were reacted in 30 mL of DMF. After heating at 80° C. overnight the resin was isolated and rinsed by the method described above.

IR (KBr, $cm^{-1}$): 3583, 3419 and 3223 (O—H), 1674 (C=O).

Example 15-3 x=2, Supported Diol SD9

This resin was prepared and isolated similarly from 1.20 g of the binaphthol monoester (x=2), 0.22 g of NaH, and 2.4 g of Merrifield's resin.

IR (KBr, $cm^{-1}$): 3451, 1690 (C=O).

EXAMPLE 16

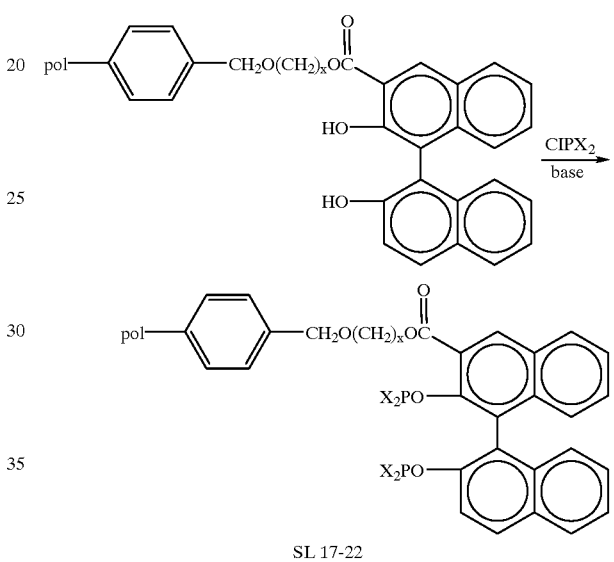

SL 17-22

The following is a general example for the synthesis of this class of supported bis(phosphite) ligands and catalysts. Examples of supported ligands and catalysts prepared by this generic route are provided in Table 1.

Example 16-1 x=4, $X_2$=1,1'-biphenoxy

The binaphthol-supported resin SD8 from Example 15-2 (2.0 g) was suspended in 10 mL of THF; 3 mL of pyridine and 2.5 g of a 50 wt % solution of 1,1'-biphenyl-2,2'-diylphosphorochloridite in toluene were then added. The yellow resin decolorized immediately. The mixture was stirred overnight at room temperature and then worked up by filtration and washing the resin with pyridine, THF, and pentane. The light yellow supported ligand SL17 was dried under vacuum.

TABLE 1

| Example | x | X2 | Supported Ligand Code |
|---------|---|----|-----------------------|
| 18-2 | x = 3 | 1,1'-biphenoxy | SL18 |
| 18-3 | x = 3 | 1,2-phenylenedioxy | SL19 |
| 18-4 | x = 4 | 1,2-phenylenedioxy | SL20 |

EXAMPLE 17

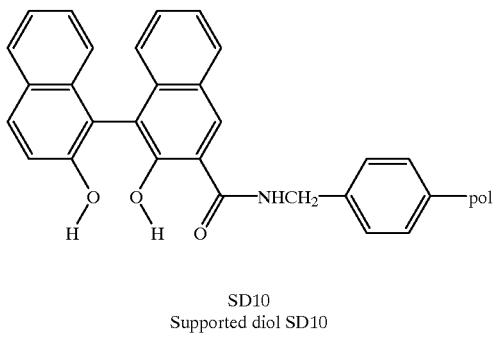

SD10
Supported diol SD10

The sulfoxyl-protected binaphthol acid chloride shown in Example 30 (5.9 g, 15 mmol) was dissolved in 150 mL of dry DMF. The commercially available benzyl amine resin (6.1 g, 6 mmol) and then diisopropyl ethyl amine (DIEA) (26 mL, 150 mmol) were added. The mixture was agitated on a Rotovap over night with exclusion of air. Water (4 mL, 220 mmol) was added to the reaction mixture and the suspension was rotated for another 3 h. The resin was filtered, washed with DMF thoroughly, then with $CH_2Cl_2$ and hexanes before vacuum drying. IR(KBr): OH and NH at 3422 $cm^{-1}$ (br) and 3535 $cm^{-1}$ (shoulder), amide at 1652 $cm^{-1}$.

EXAMPLE 18

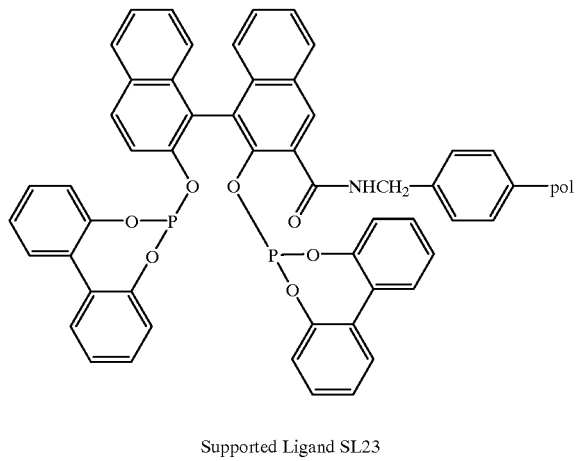

Supported Ligand SL23

DIEA (1.7 ml, 10 mmol) was added to the suspension containing the resin-supported diol SD10 (1.33 g,1.0 mmol), 2.0 g (4.0 mmol) of 1,1'-biphenyl-2,2'-diylphosphorochloridite (50% weight in toluene) and 10 ml of dry toluene. The resulting mixture was vortexed at room temperature overnight. The brown product was filtered, washed with toluene, DMF, $CH_2Cl_2$, hexanes and vacuum dried to lead to a fluffy solid.

IR(KBr): NH at 3433 $cm^{-1}$ (m), amide at 1659 $cm^{-1}$(s)

Elemental Analysis: C% 83.27, H% 6.61, N% 1.06, P% 2.12

EXAMPLE 19

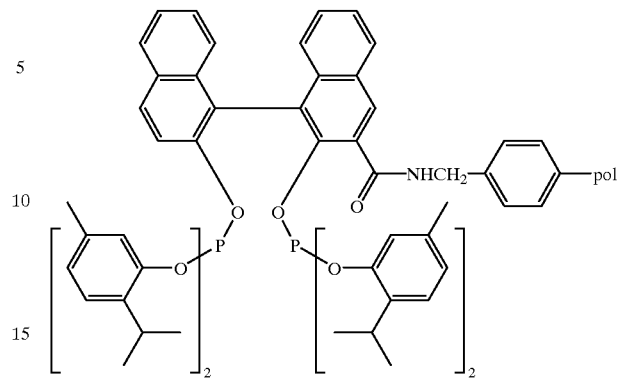

Supported Ligand SL24

This ligand was prepared according to the same procedure as that of Example 18 using 1.46 g (4.0 mmol) of bis(2-isopropyl-5-methylphenyl)-phosphorochloridite.

IR (KBr): NH at 3431 $cm^{-1}$ (m), amide at 1666 $cm^{-1}$ (s).

Elemental Analysis: C% 84.01, H% 7.07, N% 1.25, P% 1.53

EXAMPLE 20

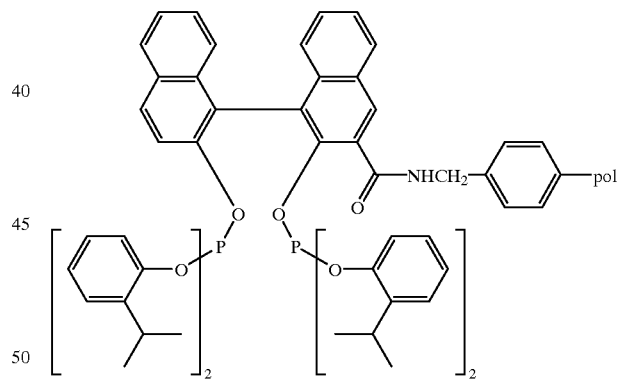

Supported Ligand SL25

This product was synthesized following the procedure described for Example 18 using 1.34 g of bis(2-isopropylphenyl)phosphorochloridite and the same amounts of the resin, DIEA and toluene.

IR (KBr): NH at 3432 $cm^{-1}$ (s), amide at 1656 $cm^{-1}$ (s)

Elemental Analysis: C% 83.25, H% 6.97, N% 1.30, P% 1.56

EXAMPLE 21

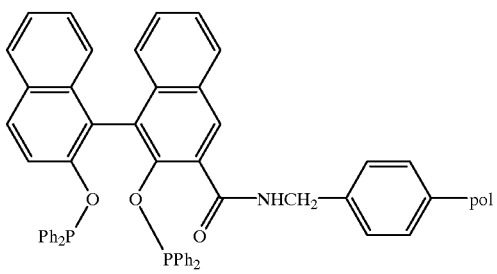

Supported Ligand SL26

The same procedure described for Example 18 was followed using 0.718 ml (4 mmol) of chlorodiphenylphosphine.

IR (KBr): NH at 3422 cm$^{-1}$ (s), amide at 1656 cm$^{-1}$ (s)

Elemental Analysis: C% 85.94, H% 6.57, N% 1.28, P% 2.01

EXAMPLE 22

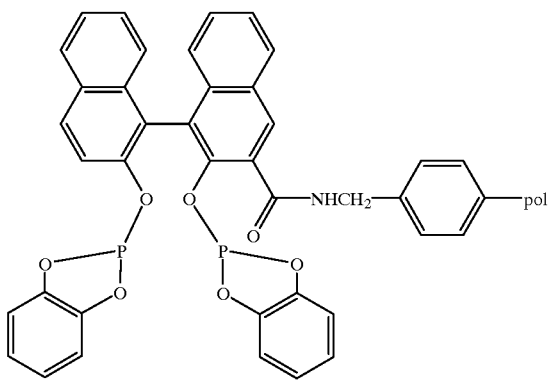

Supported Ligand SL27

This ligand was synthesized according to the same procedure as that for Example 18 using 698 mg (4.0 mmol) of 1,2-phenylenephosphorochloridite.

IR (KBr): NH at 3437 cm$^{-1}$ (m), amide at 1667 cm$^{-1}$ (s)

Elemental Analysis: C% 82.24, H% 6.26, N% 1.19, P% 2.54

EXAMPLE 23

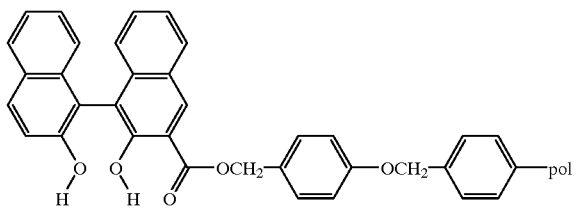

SD11
Supported Diol SD11

The same procedure described in Example 44 was employed with 10 g (6.9 mmol) of commercially available Wang resin, 8.2 g (20.7 mmol) of the sulfoxyl-protected binaphthol acid chloride shown in Example 30, and 36 ml of DIEA.

IR (KBr): OH at 3443 cm$^{-1}$ (br) ester at 1678 cm$^{-1}$ (s)

EXAMPLE 24

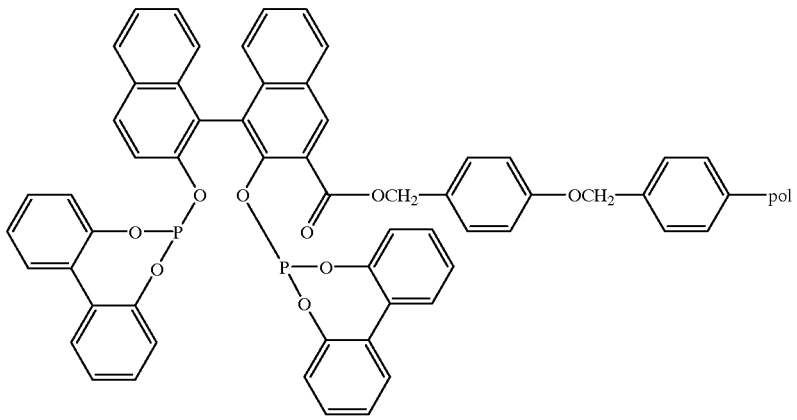

Supported Ligand SL28

This product was obtained following the same procedure described for Example 18 using 2.17 g (1.0 mmol) of resin-supported diol SD11, 2 g of 1,1'-biphenyl-2,2'-diylphosphorochloridite (50% weight in toluene, 4.0 mmol), 1.7 ml (10 mmol) of DIEA and 15 ml of anhydrous toluene.

IR (KBr): 1743 cm$^{-1}$ (vs), 1680 cm$^{-1}$ (m).

Elemental Analysis: C% 86.34, H% 7.00, P% 0.77

EXAMPLE 25

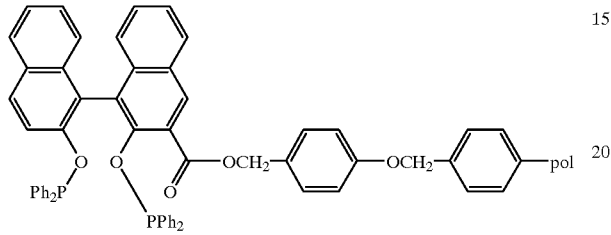

Supported Ligand SL29

This compound was made according to the procedure described for Example 18 using 2.17 g (1.0 mmol) of supported diol SD11, 884 mg (4.0 mmol) of the chlorodiphenylphosphine, 1.7 ml (10 mmol) and 15 ml of toluene.

IR (KBr): 1744 cm$^{-1}$ (m), 1680 cm$^{-1}$ (s)

Elemental Analysis: C% 86.55, H% 6.85, P% 0.59

EXAMPLE 26

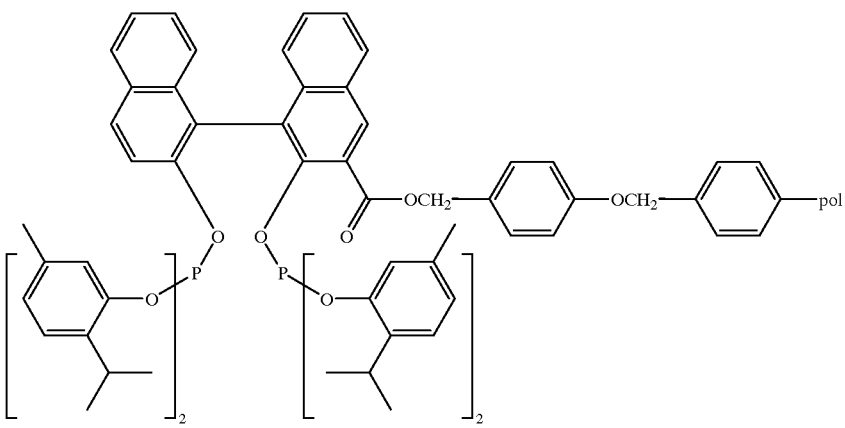

Supported Ligand SL30

The same procedure described for Example 18 was followed using 2.17 g (1.0 mmol) of the resin SD11, 1.46 g (4.0 mmol) of bis(2-isopropyl-5-methyl-phenyl)phosphorochloridite, 1.7 ml (10 mmol) of DIEA and 15 ml of toluene.

IR (KBr): 1744 cm$^{-1}$ (vs), 1680 cm$^{-1}$ (m)

Elemental Analysis: C% 85.49, H% 7.04, P% 0.64

EXAMPLE 27

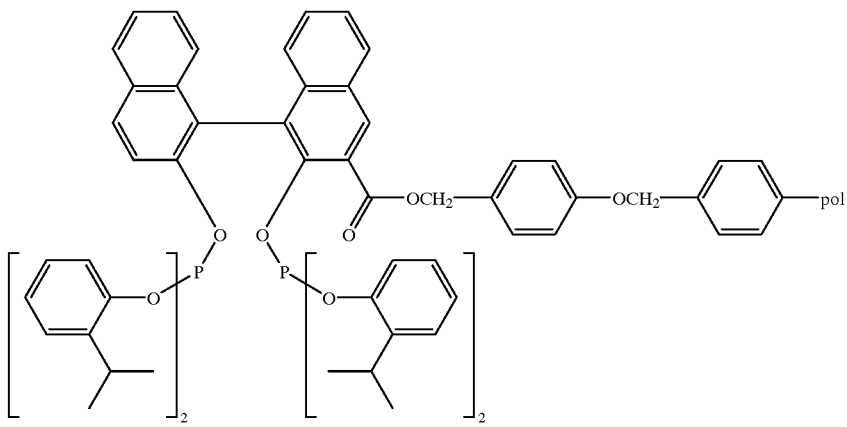

Supported Ligand SL31

The same procedure described for Example 18 was followed using 2.17 g (1.0 mmol) of supported diol SD11, 1.34 g (4.0 mmol) of bis(2-isopropylphenyl)-phosphorochloridite, 1.7 ml (10 mmol) of DIEA and 15 ml of toluene.

IR (KBr): 1722 cm$^{-1}$ (w), 1678 cm$^{-1}$ (m)

Elemental Analysis: C% 86.51, H% 7.12, P% 0.42

EXAMPLE 28

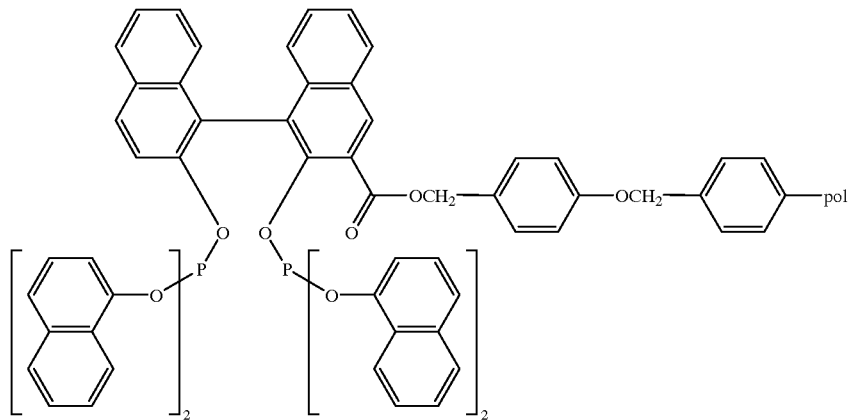

Supported Ligand SL32

This ligand was made following same procedure described for Example 18 from 2.17 g (1.0 mmol) of the supported diol SD11, 1.41 g (4.0 mmol) of bis(1-naphthyl) phosphorochloridite, 1.7 ml (10 mmol) of DIEA and 14 ml of toluene.

IR (KBr): 1726 cm$^{-1}$ (m), 1674 cm$^{-1}$ (w)

Elemental Analysis: C% 84.97, H% 8.23, P% 0.55

EXAMPLE 29

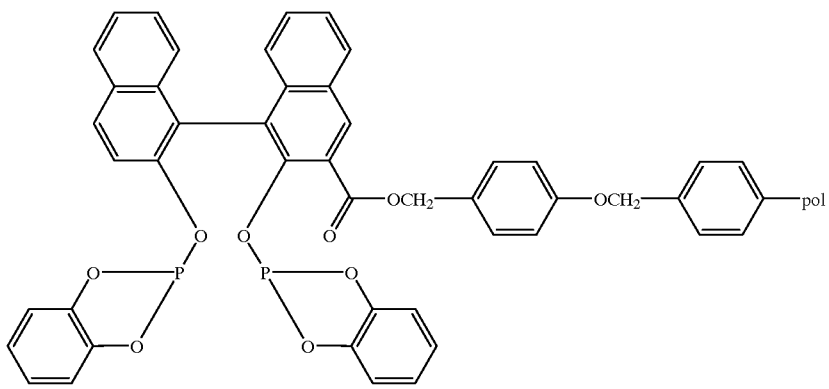

Supported Ligand SL33

The same procedure described for Example 18 was followed using 2.17 g (1.0 mmol) of the resin-supported diol SD11, 884 mg (4.0 mmol) of 1,2-phenylenephosphorochloridite, 1.7 ml (10 mmol) of DIEA and 14 ml of toluene.

IR (KBr): 1726 cm$^{-1}$ (m), 1674 cm$^{-1}$ (w)

Elemental Analysis: C% 85.35, H% 6.57, P% 0.51

EXAMPLE 30

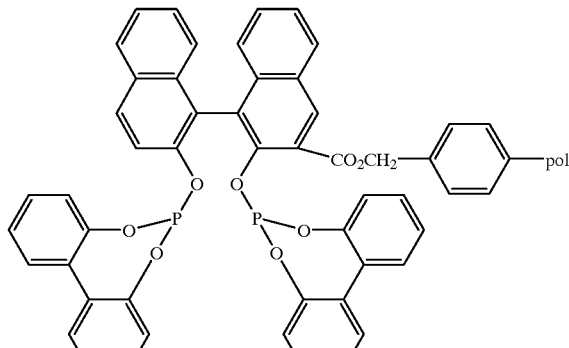

Supported Ligand SL34

The ligand was prepared following the same procedure described for Example 18 using 1.17 g (1.0 mmol) of supported diol SD5, 2 g (50% weight in toluene) (4.0 mmol) of 1,1'-biphenyl-2,2'-diylphosphorochloridite, 1.7 ml (10 mmol) of DIEA and 10 ml of toluene.

IR (KBr): 1742 cm$^{-1}$ (vs), 1680 cm$^{-1}$ (m)

Elemental Analysis: C% 84.69, H% 6.51, P% 1.03

EXAMPLE 31

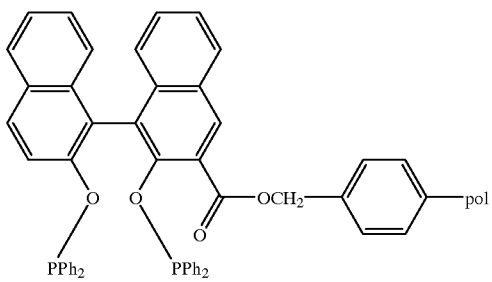

Supported Ligand SL35

The same procedure described for Example 18 was followed using 1.17 g (1.0 mmol) of supported diol SD5, 884 mg (4.0 mmol) of ClPPh$_2$, 1.7 ml (10 mmol) of DIEA and 10 ml of toluene.

IR (KBr): 1741 cm$^{-1}$ (vs)

Elemental Analysis: C% 85.45, H% 6.74, P% 1.14

EXAMPLE 32

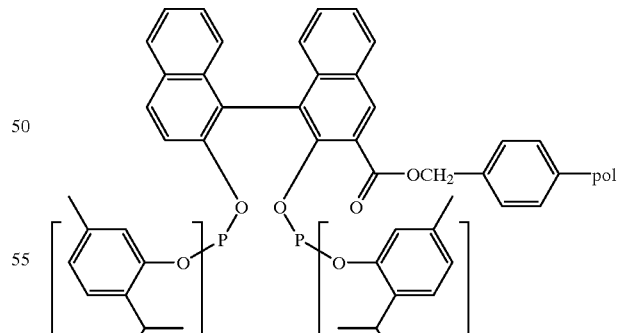

Supported Ligand SL36

This product was synthesized according to the same procedure as that for Example 18 was from 2.35 g (2.0 mmol) of the resin supported diol SD5, 2.91 g (8.0 mmol) of bis(2-isopropyl-5-methylphenyl)phosphorochloridite, 3.4 ml (10 mmol) of DIEA and 20 ml of toluene.

IR (KBr): 1741 cm$^{-1}$ (vs), 1684 cm$^{-1}$ (w)

Elemental Analysis: C% 84.62, H% 6.92, P% 0.79

EXAMPLE 33

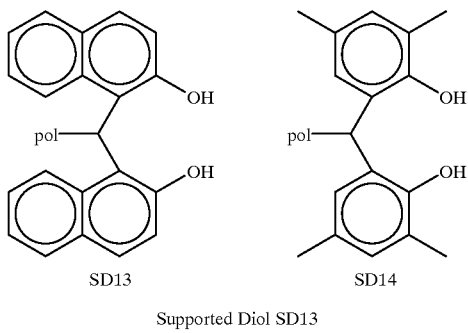

Supported Diol SD13

The resin-supported benzaldehyde described in Example 1 (407 mg, 0.5 mmol), 2-naphthol (576 mg, 2 mmol), glacial acetic acid (5 ml), CHCL$_3$ (1 ml) and hydrochloric acid (0.5 ml) were mixed with a vortexer for 5 days. The product was filtered, washed with aqueous THF, and then THF thoroughly before vacuum drying.

EXAMPLE 34

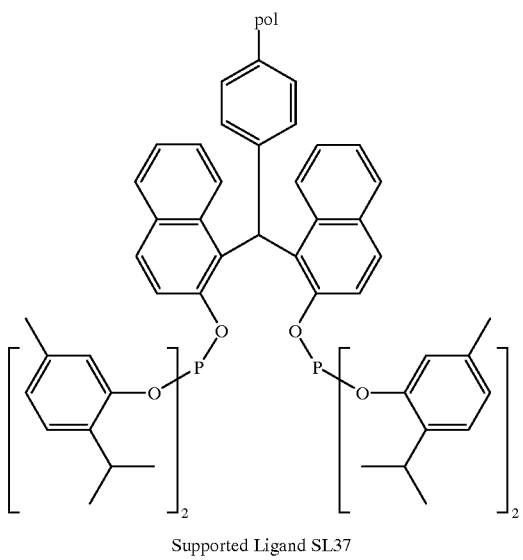

Supported Ligand SL37

The same procedure described for Example 18 was followed using 2.17 g (2.0 mmol) of supported diol SD13, 2.91 g (8.0 mmol) of bis(2-isopropyl-5-methylphenyl) phosphorochloridite, 3.4 ml (10 mmol) of DIEA and 10 ml of toluene.

Elemental Analysis: C% 90.40, H% 7.26, P% 0.61

EXAMPLE 35

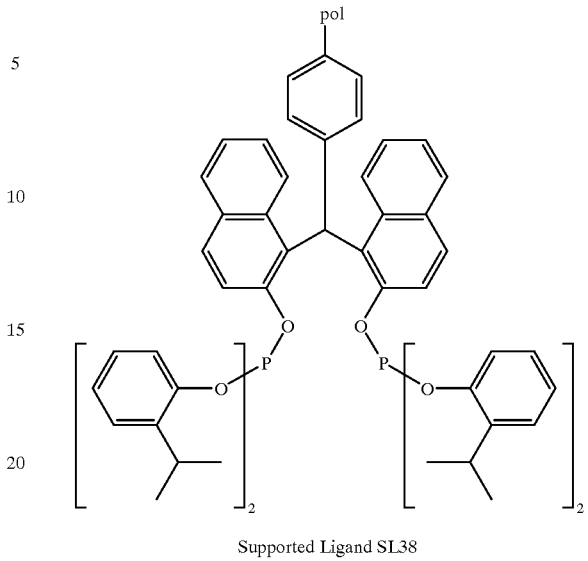

Supported Ligand SL38

The same procedure described for Example 18 was followed using 2.17 g (2.0 mmol) of the resin SD13, 2.69 g (8.0 mmol) of bis(2-isopropylphenyl)-phosphorochloridite, 3.4 ml (10 mmol) of DIEA and 10 ml of toluene.

Elemental Analysis: C% 90.10, H% 7.15, P% 0.48

EXAMPLE 36

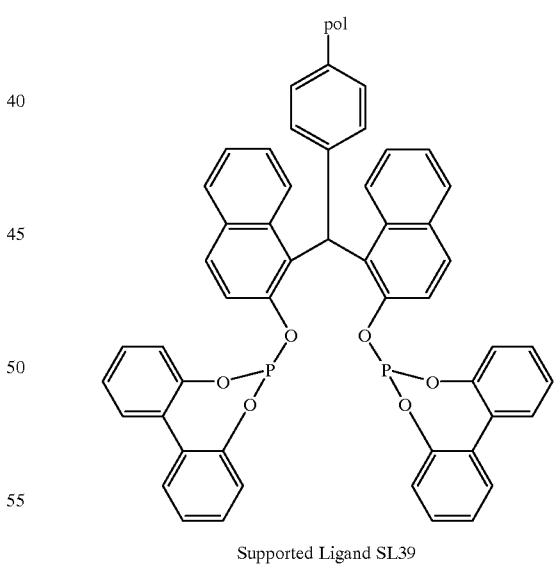

Supported Ligand SL39

The ligand was prepared according to the procedure described for Example 18 from 2.17 g (2.0 mmol) of resin SD13, 2 g of 1,1'-biphenyl-2,2'-diylphosphorochloridite (50 wt % solution in toluene, 8.0 mmol), 3.4 ml (10 mmol) of DIEA, and 20 ml of toluene.

Elemental Analysis: C% 90.28, H% 6.97, P% 0.54

EXAMPLE 37

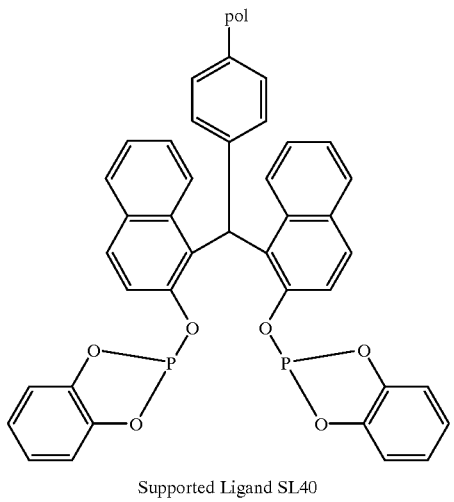

Supported Ligand SL40

The same procedure described for Example 18 was followed using 1.09 g (1.0 mmol) of resin SD13, 0.7 g (4.0 mmol) of 1,2-phenylenephosphorochloriditе, 1.7 ml (10 mmol) of DIEA, and 10 ml of toluene.

Elemental Analysis: C% 89.82, H% 6.35, P% 1.19

EXAMPLE 38

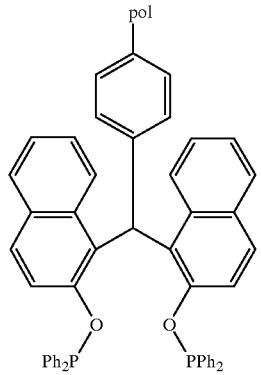

Supported Ligand SL41

This product was obtained according to the same procedure described for Example 18 using 2.17 g (2.0 mmol) of resin SD13, 1.77 g (8.0 mmol) of PPh$_2$Cl, 3.4 ml (10 mmol) of DIEA, and 10 ml of toluene.

Elemental Analysis: C% 89.90, H% 7.46, P% 0.81

EXAMPLE 39

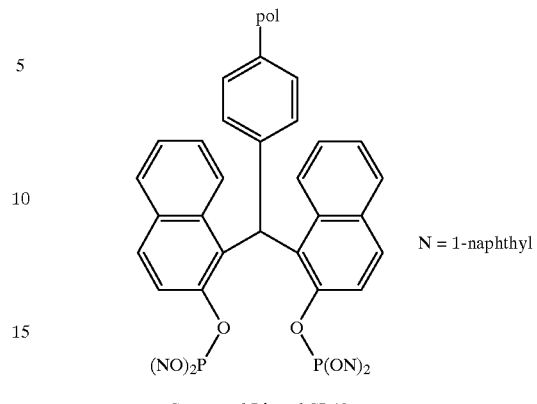

Supported Ligand SL42

The same procedure described for Example 18 was followed using 2.17 g (2.0 mmol) of resin SD13, 2.82 g (8.0 mmol) of bis(1-naphthyl)phosphorochloridite, 3.4 ml (10 mmol) of DIEA, and 20 ml of toluene.

Elemental Analysis: C% 90.34, H% 7.38, P% 0.43

EXAMPLE 40

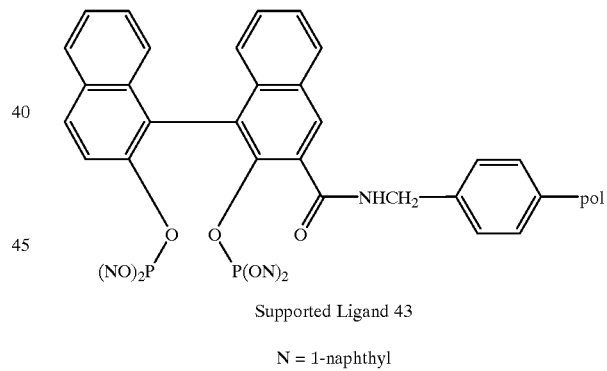

Supported Ligand 43

N = 1-naphthyl

The same procedure described for Example 18 was followed using 1.79 g (1.35 mmol) of supported diol resin SD10, 1.9 g (5.4 mmol) of bis(1-naphthyl)-phosphorochloridite, 2.3 ml (10 mmol) of DIEA, and 15 ml of toluene.

IR (KBr): NH at 3436 cm$^{-1}$ (m), amide at 1668 cm$^{-1}$ (s)

Elemental Analysis: C% 83.99, H% 6.65, N% 1.22, P% 1.60

EXAMPLE 41

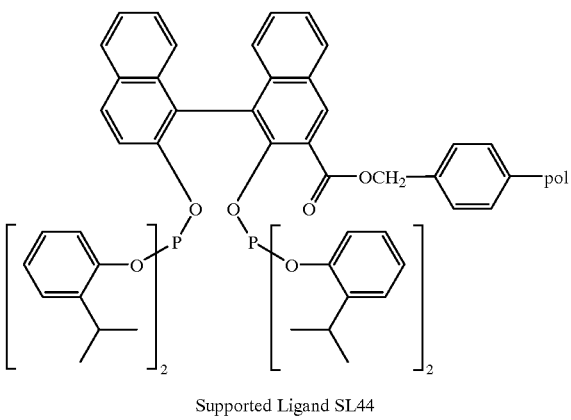

Supported Ligand SL44

The same procedure described for Example 18 was followed using 2.35 g (2.0 mmol) of the supported diol resin SD5, 2.69 g (8.0 mmol) of bis(2-isopropylphenyl) phosphorochloridite, 3.4 ml (10 mmol) of DIEA, and 20 ml of toluene.

IR (KBr): 1738 cm$^{-1}$ (s), 1676 cm$^{-1}$ (s)

Elemental Analysis: C% 83.78, H% 6.49, P% 1.00

EXAMPLE 42

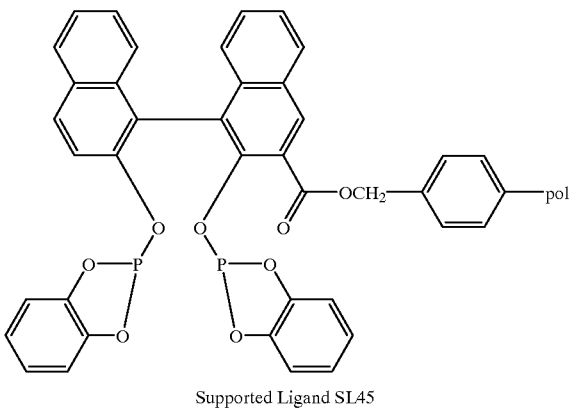

Supported Ligand SL45

The same procedure described for Example 18 was followed using 2.35 g (2.0 mmol) of resin SD5, 2.69 g (8.0 mmol) of 1,2-phenylenephosphorochloridite, 3.4 ml (10 mmol) of DIEA and 20 ml of toluene.

IR (KBr): 1739 cm$^{-1}$ (s), 1656 cm$^{-1}$ (s)

Elemental Analysis: C% 83.00, H% 6.26, P% 1.70

EXAMPLE 43

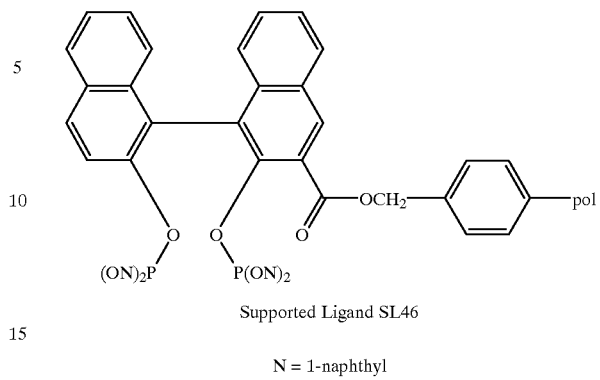

Supported Ligand SL46

N = 1-naphthyl

The same procedure described for Example 18 was followed using 2.35 g (2.0 mmol) of resin SD5, 2.82 g (8.0 mmol) of bis(1-naphthyl)phosphorochloridite, 3.4 ml (10 mmol) of DIEA, and 20 ml of toluene.

IR (KBr): 1739 cm$^{-1}$ (vs), 1681 cm$^{-1}$ (m)

Elemental Analysis: C% 84.38, H% 6.94, P% 1.25

EXAMPLE 44

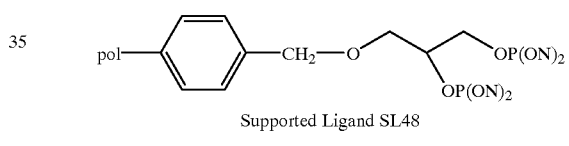

Supported Ligand SL48

N = 1-naphthyl

This supported bis(phosphite) was prepared following the same procedure described in Example 12 using bis(1-naphthyl)phosphorochloridite and supported diol SD6.

Elemental Analysis: C% 85.81, 85.99; H% 7.16; 7.39; P% 0.96

EXAMPLE 45

Supported Diol SD14

2,4-Dimethylphenol (6.95 ml, 57.6 mmol) and the resin-supported benzaldehyde described in Example 1 (5.85 g, 7.2 mmol) were added to an ice cold aqueous sulfuric acid solution (H$_2$SO$_4$: 15 ml; H$_2$O 12 ml). The reaction mixture was shaken until no starting material was observed in the IR spectrum (several days). The resin was collected by filtration, washed with aqueous acetone, aqueous THF, and thoroughly with THF before vacuum drying. IR (KBr): OH at 3444 cm$^{-1}$ (br, s).

EXAMPLE 46

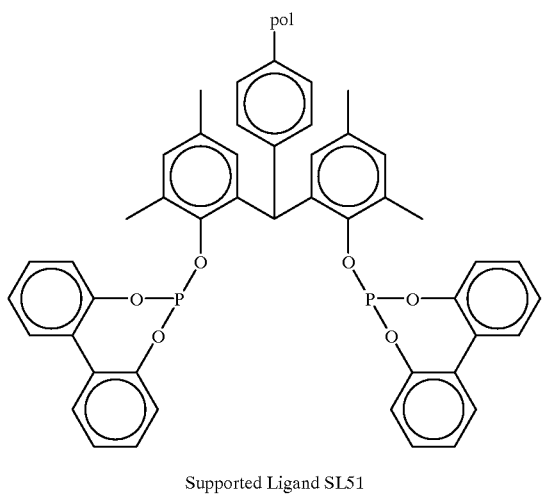

Supported Ligand SL51

This ligand was prepared according to the procedure described for Example 18 using 1.5 g (3.15 mmol) of supported diol SD14, 6.3 g (50% weight in toluene, 12.6 mmol) of 1,1'-biphenyl-2,2'-diylphosphorochloridite, 5.5 ml of DIEA and 15 ml of anhydrous toluene.

Elemental Analysis: C% 85.33, H% 7.11, P% 1.94

EXAMPLE 47

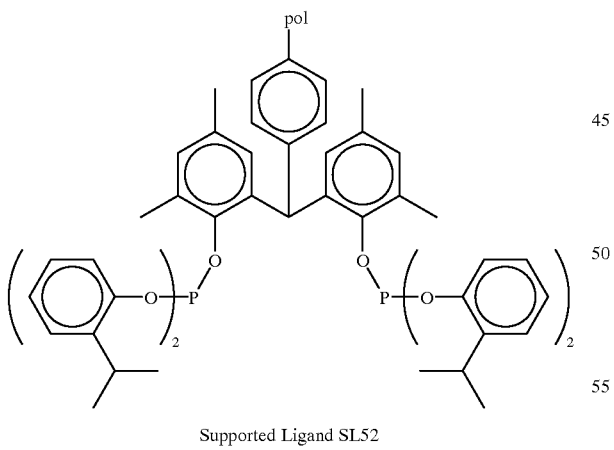

Supported Ligand SL52

This supported ligand was prepared according to the procedure described for Example 18 using 1.5 g (3.15 mmol) of supported diol SD14, 4.2 g (12.6 mmol) of bis(2-isopropylphenyl)phosphorochloridite, 5.5 ml of DIEA, and 15 ml of anhydrous toluene.

Elemental Analysis: C%85.80, H% 7.67, P% 2.56

EXAMPLE 48

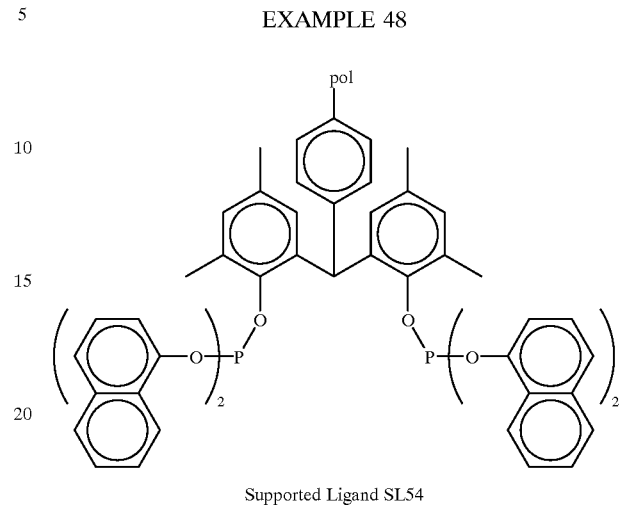

Supported Ligand SL54

This ligand was prepared according to the procedure described in Example 18 using 1.5 g (3.15 mmol) of resin SD14, 4.4 g (12.6 mmol) of bis(1-naphthyl) phosphorochloridite, 5.5 ml of DIEA and 15 ml of anhydrous toluene.

Elemental Analysis: C% 85.94, H% 7.25, P% 1.91

EXAMPLE 49

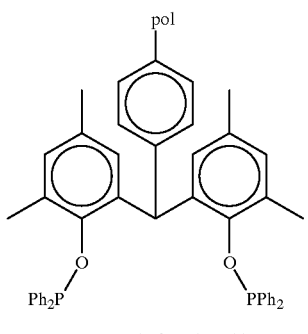

Supported Ligand SL55

This supported ligand was prepared according to the procedure described in Example 18 using 1.5 g (3.15 mmol) of resin SD14, 2.8 g (12.6 mmol) of ClPPh$_2$, 5.5 ml of DIEA and 15 ml of anhydrous toluene.

Elemental Analysis: C% 87.65, H% 7.57, P% 2.17

EXAMPLE 50

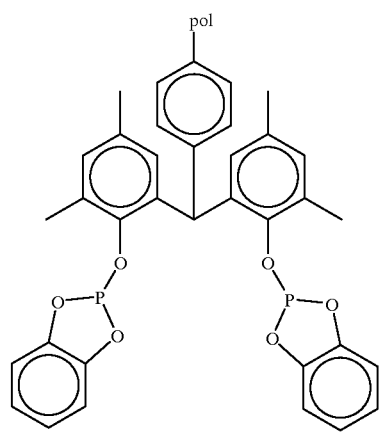

Supported Ligand SL56

This supported ligand was prepared according to the procedure described in Example 18 using 1.5 g (3.15 mmol) of supported diol SD14, 2.2 g (12.6 mmol) of 1,2-phenylenephosphorochloridite, 5.5 ml of DIEA, and 15 ml of anhydrous toluene.

Elemental Analysis: C% 84.16, H% 7.24, P% 2.41

EXAMPLE 51

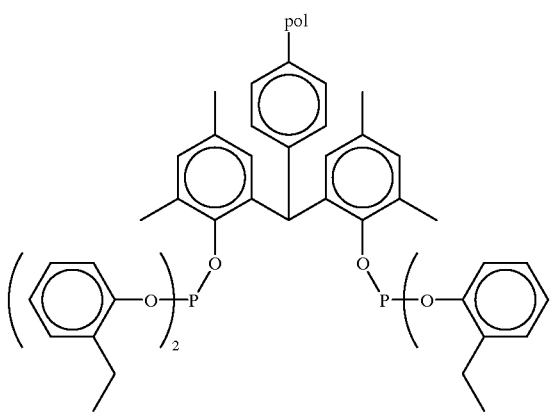

Supported Ligand SL57

This ligand was prepared according to the procedure described in Example 18 using 1.5 g (3.15 mmol) of the resin, 3.88 g (12.6 mmol) of bis(2-ethylphenyl)phosphorochloridite, 5.5 ml of DIEA and 15 ml of anhydrous toluene.

Elemental Analysis: C% 84.45, H% 7.09, P% 3.09

EXAMPLE 52

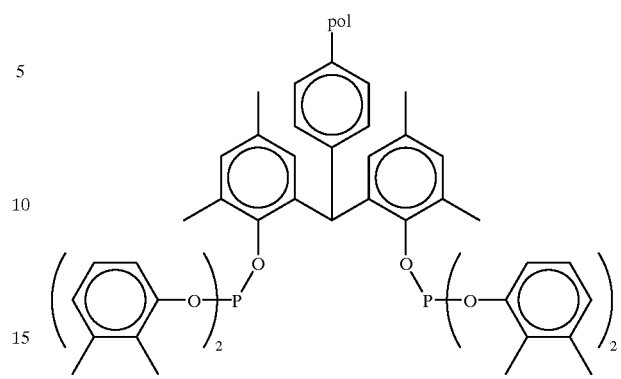

Supported Ligand SL58

This ligand was prepared according to the procedure described in Example 18 using 1.5 g (3.15 mmol) of the supported diol SD14, 3.88 g (12.6 mmol) of bis(2,3-dimethylphenyl)phosphorochloridite, 5.5 ml of DIEA, and 15 ml of anhydrous toluene.

Elemental Analysis: C% 84.97, H% 7.16, P% 2.98

EXAMPLE 53

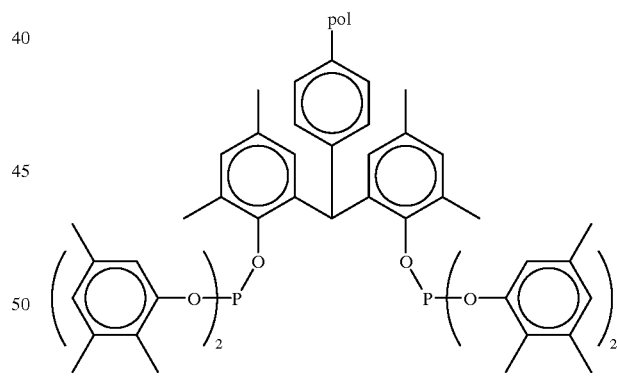

Supported Ligand SL59

This ligand was prepared according to the procedure described in Example 18 using 1.5 g (3.15 mmol) of the resin SD14, 4.23 g (12.6 mmol) of bis(2,3,5-trimethylphenyl)phosphorochloridite, 5.5 ml of DIEA, and 15 ml of anhydrous toluene.

Elemental Analysis: C% 84.65, H% 7.62, P% 2.70

EXAMPLE 54

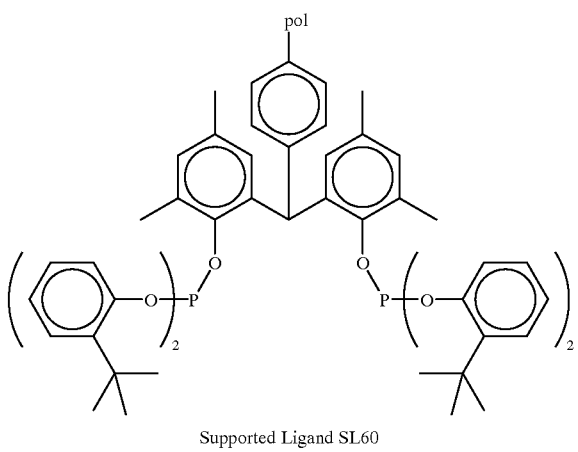

Supported Ligand SL60

This ligand was prepared according to the procedure described in Example 18 using 1.5 g (3.15 mmol) of the resin SD14, 4.60 g (12.6 mmol) of bis(2-tertbutylphenyl)phosphorochloridite, 5.5 ml of DIEA and 15 ml of anhydrous toluene.

Elemental Analysis: C% 85.83, H% 7.68, P% 2.40

EXAMPLE 55

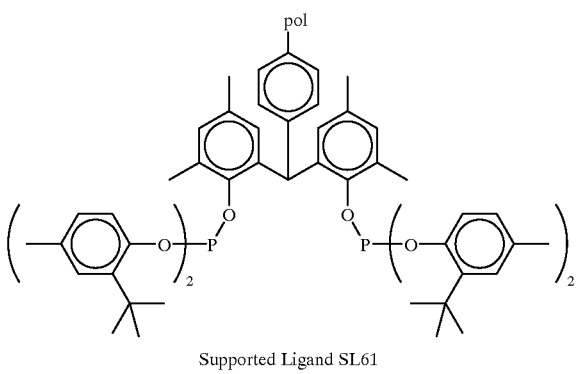

Supported Ligand SL61

This ligand was prepared according to the procedure described in Example 18 using 1.5 g (3.15 mmol) of the resin SD14, 4.95 g (12.6 mmol) of the corresponding bis(2-tertbutyl-4-methylphenyl)phosphorochloridite, 5.5 ml of DIEA and 15 ml of anhydrous toluene.

Elemental Analysis: C% 86.19, H% 7.80, P% 2.19

EXAMPLE 56

The following is a general procedure for the preparation of supported rhodium catalysts using the supported ligands described in previous examples. Information in Table 2 shows the generality of this procedure.

The appropriate supported ligand (a amount corresponding to 0.116–0.0116 mmole of contained bis(phosphite) groups) is slurried into 5 mL of dry, deoxygenated toluene. $Rh(CO)_2(acac)$ (3 mg, 0.0116 mmol, P/Rh=2–20) is added and gas evolution is noted as CO is displaced. The toluene supernatant turns colorless as the $Rh(CO)_2(acac)$ becomes loaded onto the support beads. The reuslting slurry is useful as obtained for catalytic reactions.

On the Table below I have simply listed all the ligands which correlated with Leo Manzer's hydroformylation examples, so that appropriate info on the prep of each rhodium ligand can be placed thereon.

TABLE 2

Supported $Rh(CO)_2(acac)$ Catalysts Prepared via Example 54

| Example | Supported Ligand Used | Supported Catalyst ID |
|---|---|---|
| 56-1 | SL2 | SC1 |
| 56-2 | SL3 | SC2 |
| 56-3 | SL6 | SC3 |
| 56-4 | SL12 | SC4 |
| 56-5 | SL14 | SC5 |
| 56-6 | SL15 | SC6 |
| 56-7 | SL16 | SC7 |
| 56-8 | SL17 | SC8 |
| 56-9 | SL18 | SC9 |
| 56-10 | SL19 | SC10 |
| 56-11 | SL20 | SC11 |
| 56-12 | SL23 | SC12 |
| 56-13 | SL24 | SC13 |
| 56-14 | SL25 | SC14 |
| 56-15 | SL26 | SC15 |
| 56-16 | SL27 | SC16 |
| 56-17 | SL28 | SC17 |
| 56-18 | SL29 | SC18 |
| 56-19 | SL30 | SC19 |
| 56-20 | SL31 | SC20 |
| 56-21 | SL32 | SC21 |
| 56-22 | SL33 | SC22 |
| 56-23 | SL34 | SC23 |
| 56-24 | SL35 | SC24 |
| 56-25 | SL36 | SC25 |
| 56-26 | SL37 | SC26 |
| 56-27 | SL38 | SC27 |
| 56-28 | SL39 | SC28 |
| 56-29 | SL40 | SC29 |
| 56-30 | SL41 | SC30 |
| 56-31 | SL42 | SC31 |
| 56-32 | SL43 | SC32 |
| 56-33 | SL44 | SC33 |
| 56-34 | SL45 | SC34 |
| 56-35 | SL46 | SC35 |
| 56-36 | SL48 | SC36 |
| 56-37 | SL51 | SC37 |
| 56-38 | SL52 | SC38 |
| 56-39 | SL54 | SC39 |
| 56-40 | SL55 | SC40 |
| 56-41 | SL56 | SC41 |
| 56-42 | SL57 | SC42 |
| 56-43 | SL58 | SC43 |
| 56-44 | SL59 | SC44 |
| 56-45 | SL60 | SC45 |
| 56-46 | SL61 | SC46 | acac = acetylacetonate

EXAMPLE 57

Propylene Hydroformylation with Supported Rhodium Catalysts

The resin supported ligand and Rhodium were charged as the $Rh(CO)_2(acac)$ loaded material, prepared as described in Example 56. The amount of $Rh(CO)_2acac$ added was 3 mg. The amount of supported ligand charged was targeted at a 1:1 of chelate ligand to rhodium. The reactor vessel was charged to 100 psi ($6.89 \times 10^{+5}$ Pa) with 40 psi ($2.75 \times 10^{+5}$ Pa) of propylene and 60 psi ($4.13 \times 10^{+5}$ Pa) of a 1:1 ratio of $H_2$ to CO. Typically the reaction was run for 1 hour. At the end of the run the reactor is depressurized and an aliquot of dibutylether is added as an internal standard. The liquid is analyzed by gas chromatography to give the yields of products. As used below in Table 3, Comparative examples are designated by letters and $Ph_3P$=triphenyl phosphite, and DD1=

TABLE 3

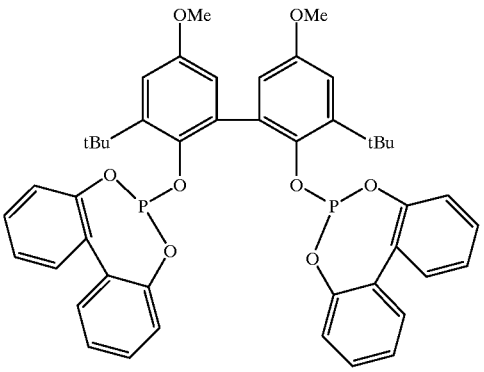

i-BA or IBA = isobutyraldehyde
n-BAL or BAL = normal butyraldehyde
TON = Turnovers, i.e. moles of product/moles of rhodium/hour Prorylene Hydroformylation

| Example | Ligand | Catalyst | i-BA Sel, % | n-BAL Sel, % | TON (IBA + BAL) |
|---|---|---|---|---|---|
| A | Ph$_2$P(CH$_2$)$_2$PPh$_2$ | | 56.3 | 43.7 | 6.7 |
| B | DP1 | | 19.6 | 80.4 | 3711.4 |
| C | DP1 | | 5.2 | 94.8 | 2586.5 |
| D | DP1 | | 14.9 | 85.1 | 1770.4 |
| E | DP1 | | 2.8 | 97.2 | 130.8 |
| F | Ph$_3$P | | 39.7 | 60.3 | 397.1 |
| G | Ph$_3$P | | 48.2 | 51.8 | 292.4 |
| H | Ph$_3$P | | 46.3 | 53.7 | 2.4 |
| 57-1 | SL55 | SC40 | 63.5 | 36.5 | 75.4 |
| 57-2 | SL54 | SC39 | 21.4 | 78.6 | 433.6 |
| 57-3 | SL43 | SC32 | 15.8 | 84.2 | 1082.7 |
| 57-4 | SL61 | SC46 | 53.7 | 46.3 | 100.7 |
| 57-5 | SL60 | SC45 | 59.6 | 40.4 | 71.7 |
| 57-6 | SL59 | SC44 | 62.2 | 37.8 | 102.5 |
| 57-7 | SL58 | SC43 | 36.2 | 63.8 | 203.7 |
| 57-8 | SL58 | SC43 | 49.7 | 50.3 | 90.6 |
| 57-9 | SL57 | SC42 | 39.0 | 61.0 | 153.0 |
| 57-10 | SL57 | SC42 | 42.7 | 57.3 | 129.6 |
| 57-11 | SL52 | SC38 | 74.7 | 25.3 | 69.4 |
| 57-12 | SL51 | SC37 | 68.1 | 31.9 | 126.6 |
| 57-13 | SL56 | SC41 | 42.6 | 57.4 | 560.5 |
| 57-14 | SL43 | SC32 | 40.5 | 59.5 | 1058.7 |
| 57-15 | SL45 | SC34 | 30.4 | 69.6 | 984.6 |
| 57-16 | SL44 | SC33 | 58.1 | 41.9 | 322.7 |
| 57-17 | SL41 | SC30 | 33.2 | 66.8 | 481.9 |
| 57-18 | SL40 | SC29 | 62.3 | 37.7 | 114.7 |
| 57-19 | SL39 | SC28 | 54.4 | 45.6 | 952.1 |
| 57-20 | SL37 | SC26 | 19.1 | 80.9 | 1206.6 |
| 57-21 | SL38 | SC27 | 31.9 | 68.1 | 1604.2 |
| 57-22 | SL36 | SC25 | 20.4 | 79.6 | 2158.7 |
| 57-23 | SL35 | SC24 | 28.1 | 71.9 | 1066.7 |
| 57-24 | SL34 | SC23 | 72.0 | 28.0 | 20.8 |
| 57-25 | SL28 | SC17 | 69.0 | 31.0 | 13.1 |
| 57-26 | SL31 | SC20 | 50.4 | 49.6 | 42.8 |
| 57-27 | SL30 | SC19 | 61.3 | 38.7 | 30.4 |
| 57-28 | SL29 | SC18 | 60.0 | 40.0 | 45.0 |
| 57-29 | SL33 | SC22 | 18.6 | 81.4 | 225.2 |
| 57-30 | SL32 | SC21 | 49.5 | 50.5 | 51.7 |
| 57-31 | SL25 | SC14 | 54.0 | 46.0 | 10.9 |
| 57-32 | SL24 | SC13 | 52.5 | 47.5 | 7.5 |
| 57-33 | SL27 | SC16 | 98.1 | 1.9 | 16.5 |
| 57-34 | SL26 | SC15 | 100.0 | 0.0 | 15.1 |
| 57-35 | SL23 | SC12 | 100.0 | 0.0 | 11.3 |
| 57-36 | SL42 | SC31 | 50.6 | 49.4 | 153.2 |
| 57-37 | SL46 | SC35 | 44.3 | 55.7 | 283.8 |
| 57-38 | SL48 | SC36 | 45.1 | 54.9 | 129.7 |
| 57-39 | SL16 | SC7 | 31.3 | 68.7 | 2080.2 |
| 57-40 | SL14 | SC5 | 52.2 | 47.8 | 3.6 |
| 57-41 | SL20 | SC11 | 46.4 | 53.6 | 98.8 |
| 57-42 | SL19 | SC10 | 64.5 | 35.5 | 72.1 |
| 57-43 | SL17 | SC8 | 33.5 | 66.5 | 387.1 |
| 57-44 | SL18 | SC9 | 55.0 | 45.0 | 57.9 |

TABLE 3-continued

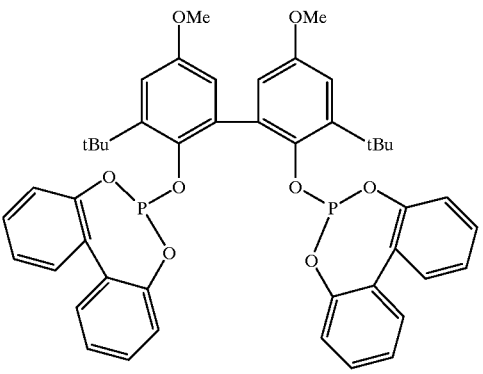

i-BA or IBA = isobutyraldehyde
n-BAL or BAL = normal butyraldehyde
TON = Turnovers, i.e. moles of product/moles of rhodium/hour Propylene Hydroformylation

| Example | Ligand | Catalyst | i-BA Sel, % | n-BAL Sel, % | TON (IBA + BAL) |
|---|---|---|---|---|---|
| 57-56 | SL6 | SC3 | 36.5 | 63.5 | 111.4 |
| SL3 | SL3 | SC2 | 26.9 | 73.1 | 264.8 |
| 57-58 | SL2 | SC1 | 34.2 | 65.8 | 131.6 |
| 57-59 | SL15 | SC6 | 56.8 | 43.2 | 8.3 |
| 57-60 | SL12 | SC4 | 7.9 | 92.1 | 1450.3 |

EXAMPLE 58

Propylene Hydroformylation—Vapor Phase

An empty 0.64 cm diameter, 37.5 cm long stainless steel tubular reactor was placed in a nitrogen-filled glove box. A plug of glass wool was placed in the bottom end of the reactor, followed by the amount and type of catalyst shown in Table 4. The catalyst in each case was pre-mixed with glass beads to dilute it within the reactor. A thermocouple was inserted into the top of the reactor. Both ends of the reactor were sealed with metal fittings, and the reactor was removed from the glove box and was connected to stainless steel reactor feed lines purged with nitrogen. The reactor was equipped with a by-pass line to allow for a flow of CO and $H_2$ to be established before opening the inlet side of the reactor to feed gases. The desired temperature of 100° C. was established in the reactor by means of a split tube furnace surrounding the reactor. When the desired flow rates of CO and $H_2$ feed gases had been achieved, a valve was turned on to begin passing CO and $H_2$ over the catalyst. Periodically, at times shown in Table 4. The reactor effluent samples were analyzed by gas chromatography for the amounts of unreacted propylene, linear and branched butyraldehyde.

Examples 58-1 to 58-6 were all run at 100° C., with feeds of 4 cc each of CO, $H_2$ and propylene, except as noted, and at a total pressure of 100 psig. Table 4 shows the grams of catalyst and the weight percent of phosphorus in each catalyst used. The mole ratios of Rh/P shown in Table 4 are the ratios used to complex Rh to each catalyst from a solution of Rh(acetonylacetonate) $(CO)_2$, before several rinsing times with toluene to remove uncomplexed Rh. Final Rh/P ratios should have been close to 0.5. The TON/hr numbers shown in Table 4 were calculated to represent the moles of propylene reacted per mole of Rh per hour. Example 58-6 was run using DP1 dispersed on carbon.

TABLE 4

Gas Phase Propylene CO/H2 Reactions

| Ex. No. | Ligand | Catalyst g, % P, Rh/P | Silica Beads, g | Propylene/CO/H2 cc/min. | Elapsed Time, hr. | Propylene % Conv. | Linear/ Branched | TON/hr |
|---|---|---|---|---|---|---|---|---|
| 58-1 | SL24 | 0.25, 1.52, 1.26 | 0.27 | 4/4/04 | 1 | 5.1 | 1.5 | 3.5 |
| | | | | | 4 | 7.1 | 3.1 | 4.9 |
| | | | | | 10 | 10.8 | 2.5 | 7.5 |
| | | | | | 16 | 7.9 | 3.0 | 5.5 |
| | | | | | 21 | 9.4 | 3.4 | 6.5 |
| | | | | | 24 | 8.6 | 3.8 | 5.9 |
| 58-2 | SL25 | 0.25, 1.56, 1.22 | 0.53 | 4/4/04 | 1 | 7.3 | 2.0 | 5.1 |
| | | | | | 4 | 8.2 | 2.5 | 5.7 |
| | | | | | 10 | 7.8 | 2.6 | 5.5 |

TABLE 4-continued

Gas Phase Propylene CO/H2 Reactions

| Ex. No. | Ligand | Catalyst g, % P, Rh/P | Silica Beads, g | Propylene/CO/H2 cc/min. | Elapsed Time, hr. | Propylene % Conv. | Linear/ Branched | TON/hr |
|---|---|---|---|---|---|---|---|---|
| | | | | | 16 | 8.7 | 3.3 | 6.1 |
| | | | | | 21 | 5.2 | 3.8 | 3.6 |
| | | | | | 23 | 4.6 | 4.1 | 3.2 |
| 58-3 | SL52 | 0.28, 2.56, 0.88 | 0.50 | 4/4/04 | 1 | 9.7 | 3.0 | 6.1 |
| | | | | | 10 | 20.6 | 4.5 | 13.0 |
| | | | | | 20 | 70.0 | 8.4 | 44.1 |
| | | | | | 29 | 52.9 | 9.5 | 33.4 |
| | | | | | 41 | 64.4 | 10.0 | 40.6 |
| | | | | | 50 | 68.8 | 9.8 | 43.4 |
| | | | | | 59 | 72.6 | 9.9 | 45.8 |
| | | | | | 71 | 77.3 | 10.3 | 48.7 |
| | | | | | 82 | 81.0 | 12.5 | 51.0 |
| | | | | | 91 | 78.7 | 10.6 | 49.6 |
| | | | | | 100 | 79.0 | 10.5 | 49.8 |
| | | | | | 109 | 79.7 | 10.8 | 50.2 |
| | | | | | 118 | 71.5 | 10.0 | 45.1 |
| 58-5 | SL51 | 0.21, 1.94, 0.81 | 0.51 | 4/4/04 | 1 | 1.6 | 2.0 | 2.0 |
| | | | | | 10 | 12.9 | 2.6 | 15.6 |
| | | | | | 19 | 15.3 | 3.3 | 18.5 |
| | | | | | 31 | 12.1 | 3.2 | 14.7 |
| | | | | | 40 | 13.7 | 3.3 | 16.6 |
| | | | | | 49 | 12.2 | 3.3 | 14.7 |
| | | | | | 61 | 14.0 | 3.3 | 16.9 |
| | | | | | 70 | 12.7 | 3.4 | 15.4 |
| | | | | | 79 | 12.5 | 3.4 | 15.1 |
| | | | | | 91 | 14.7 | 3.4 | 17.8 |
| | | | | | 100 | 14.9 | 3.5 | 18.0 |
| | | | | | 109 | 15.6 | 3.5 | 18.9 |
| | | | | | 121 | 16.3 | 3.5 | 19.8 |
| | | | | | 127 | 13.2 | 3.5 | 16.0 |
| 58-6 | DP1 | 0.10, 0.33, 0.26 | 0.50 | 4/4/04 | 1 | 21.1 | 20.6 | 795 |
| | | | | | 2 | 20.4 | 23.1 | 768 |
| | | | | | 3 | 17.4 | 24.5 | 653 |
| | | | | | 4 | 16.3 | 24.7 | 613 |
| | | | | | 5 | 14.7 | 24.9 | 553 |
| | | | | | 6 | 14.4 | 24.7 | 541 |
| | | | | | 9 | 15.0 | 24.6 | 564 |
| | | | | | 12 | 12.1 | 24.3 | 457 |
| | | | | | 15 | 10.0 | 24.3 | 376 |
| | | | | | 18 | 9.5 | 24.3 | 356 |
| | | | | | 21 | 7.2 | 24.2 | 272 |
| | | | | | 24 | 8.1 | 24.2 | 306 |

EXAMPLE 59

Preparation of a Supported Disubstituted Binaphthol

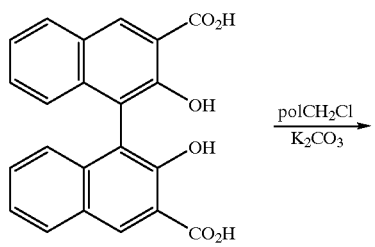

polCH₂Cl
K₂CO₃ →

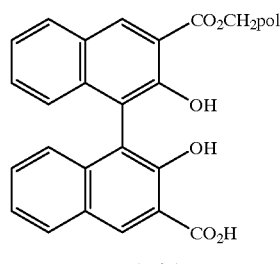

Supported Diol SD14

A mixture of 50 g (60 mmol) of Merrifield resin (polCH₂Cl) 2,2'-dihydroxy-1,1'-binaphthalene-3,3'-dicarboxylic acid (33.7 g), potassium carbonate (12.4 g) and DMF (350 ml) was heated at 90° C. with stirring for 8 hrs. The color of the resin changed from white to greenyellow. The mixture was diluted with water, filtered, washed with H2O, DMF, and acetone, and then thoroughly dried in the air to give the desired product. IR (KBr, cm$^{-1}$): 1712 (vs), 1676 (vs).

Enablement references for this synthesis:
1. Hetet, C. L., David, M., Carreaux, F., Carboni, B. and Sauleau, A., Tetrahedron Lett., 1997, 38(29), 5153–5156.
2. Gisin, B. F. Helv. Chim. Acta 1973, 56, 1476–1482.

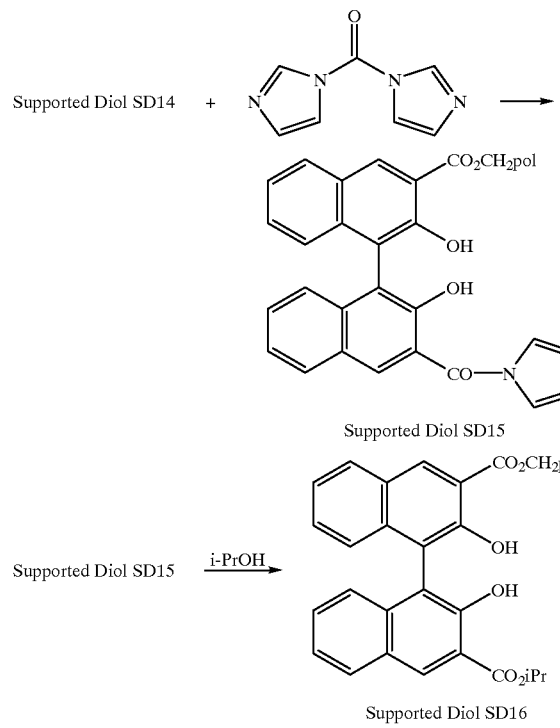

Preparation of Supported Diols SD15 and SD16. Supported diol SD14 (5 g) was swollen in 50 ml of anhydrous DMF. 1,1'-Carbonyldiimidazole (689 mg) was added. The mixture was shaken overnight. The resin was filtered, and washed with DMF (3×) to give diol SD15. IR (KBr, cm$^{-1}$): 1772 (s), 1720 (s). Next, DMF (25 ml) and i-PrOH (1.6 ml) were added. The mixture was shaken overnight, then filtered, washed with DMF (3×), acetone (3×) and dried in the air to give supported diol SD16, which is the desired supported unsymmetrical diester diol. IR (KBr, cm$^{-1}$): 1762 (s), 1713 (vs), 1676 (vs).

Enablement reference:
Bodanszky, M., Bodanszky, A. in "The Practice of Peptide Synthesis" Springer-Verlag, Berlin Heidelberg, 1994, p. 122.

EXAMPLE 60

Preparation of a Supported Bis(Phosphite) using Supported Diol SD16

Supported diol SD16 (1.8 g) was swollen in 15 ml of anhydrous toluene. Bis(2-isopropylphenyl) phosphorochloridite (1.48 g) and then DIEA (1.1 ml) were added. The suspension was shaken overnight. The resin was collected by filtration, washed with toluene (3×), DMF (3×), THF (3×), hexanes and then dried in the air to give the supported bis(phosphite) (SL62) as white beads. Elemental Analysis: P=0.99 wt. %.

The supported bis(phosphite) ligands shown in the Table below were prepared in a similar manner.

TABLE 5

Supported bis(phosphite) ligands derived from SD16

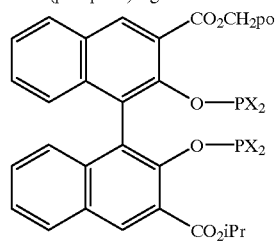

| Example No. | X | Supported Ligand ID | Analysis wt % P |
|---|---|---|---|
| 60-1 | O-2-ipr-5-MeC$_6$H$_3$ | SL63 | 0.72 |
| 60-2 | O-2-OMe-4-MeC$_6$H$_3$ | SL64 | 1.49 |
| 60-3 | O-2,4-Me$_2$C$_6$H$_3$ | SL65 | 1.40 |
| 60-4 | O-2,3,5-Me$_3$C$_6$H$_2$ | SL66 | 1.03 |
| 60-5 | O-2-EtC$_6$H$_4$ | SL67 | 1.31 |
| 60-6 | O-2,3-Me$_2$C$_6$H$_3$ | SL68 | 1.0 |
| 60-7 | O-1-naphthyl | SL69 | 1.07 |
| 60-8 | OC$_6$H$_5$ | SL70 | 1.20 |
| 60-9 | 1,2-phenylenedioxy | SL71 | 1.64 |
| 60-10 | O-3-MeC$_6$H$_4$ | SL72 | 1.29 |
| 60-11 | C$_6$H$_5$ | SL73 | 1.67 |
| 60-12 | O-2-MeC$_6$H$_4$ | SL74 | 0.81 |
| 60-13 | O-2-tBuC$_6$H$_4$ | SL75 | 0.88 |
| 60-14 | O-2-tBu-4-MeC$_6$H$_3$ | SL76 | 1.02 |
| 60-15 | 1,1'-biphenyl-2,2'-dioxy | SL77 | 1.02 |

EXAMPLE 61

Hydroformylation of Methyl 3-Pentenoate

A 25 mL glass lined pressure vessel was charged with 5 mL of a solution containing 11.4 g (100 mmol) methyl-3-pentenoate, 0.068 g (0.2 mmol) of Rh(CO)$_2$(acac), and 1.00 g of tetradecane (internal GC standard) in 100 mL toluene. 1.0 equiv (0.2 mmol) of polymer-supported bisphosphite was also added to the vessel. The ratio of ligand to Rh was 1 (P:Rh=2). The pressure vessel was freed from air by purging first with nitrogen (twice) and then with 1:1 CO/H$_2$ (twice). The vessel was then pressurized to 0.5 MPa CO and heated to 100° C. with agitation for 2 hours. The heat was shut off and the pressure vessel was allowed to cool to room temperature. The excess gases were vented and the products were analyzed by gas chromatography on a 30 M DB-Wax® capillary GC column. The results are shown in the Table below:

TABLE 6

Methyl 3-Pentenoate (M3P) Hydroformylation

| Example | Supported Ligand ID | M3P Conversion | Linearity, % | % MV | % M2P |
|---|---|---|---|---|---|
| Comparative Example | no P ligand used | 41.7 | 39.3 | 0.6 | 26.1 |
| 61-1 | SL62 | 95.8 | 52.9 | 8.5 | 15.8 |
| 61-2 | SL63 | 97.0 | 88.9 | 10.6 | 7.2 |
| 61-3 | SL67 | 97.4 | 86.2 | 11.1 | 5.5 |
| 61-4 | SL68 | 98.0 | 85.4 | 10.2 | 8.3 |
| 61-5 | SL69 | 93.5 | 88.0 | 7.5 | 8.5 |
| 61-6 | SL71 | 17.9 | 53.1 | 0.5 | 4.6 |
| 61-7 | SL72 | 97.5 | 62.1 | 7.4 | 5.6 |
| 61-8 | SL74 | 96.5 | 60.3 | 8.7 | 10.6 |

TABLE 6-continued

Methyl 3-Pentenoate (M3P) Hydroformylation

| Example | Supported Ligand ID | M3P Conversion | Linearity, % | % MV | % M2P |
|---------|---------------------|----------------|--------------|------|-------|
| 61-9    | SL75                | 67.0           | 54.3         | 3.7  | 14.7  |
| 61-10   | SL76                | 40.9           | 63.0         | 2.2  | 10.7  |
| 61-11   | SL64                | 96.7           | 57.2         | 4.7  | 3.7   |
| 61-12   | SL65                | 97.3           | 62.3         | 8.7  | 5.5   |
| 61-13   | SL66                | 99.5           | 75.1         | 12.5 | 2.3   |
| 61-14   | SL70                | 92.8           | 65.2         | 6.5  | 9.9   |

MV = methyl valerate; M2P = methyl 2-pentenoate

EXAMPLE 62

Hydroformylation of 3-Pentenenitrile and Methyl 4-Pentenoate

Supported rhodium catalysts are prepared by treating a suspension of the supported ligand in toluene with Rh(CO)$_2$(acac) so as to give a P/Rh ratio of 10:1. The resulting rhodium-loaded support is then activated by treatment at 95° C. and 75 psi H$_2$/CO (1:1) for 1 h before cooling to room temperature. The resulting activated catalyst thus obtained is suitable for catalytic hydroformylation.

The supported rhodium catalysts prepared according to this procedure were used for 3PN hydroformylation catalysis in the following manner. To a suspension of the supported catalyst in toluene (5 mL, 200 ppm Rh, 1 0/1 P/Rh) is added sufficient 3PN to give a 1 M solution. The reactor is then heated to 95° C. under 75 psi of CO/H$_2$. After 2 h the reactor is cooled to room temperature, vented, and the supernatant is decanted and analyzed by gas chromatography on a Quadrex-23 Capillary column. These results are summarized in Table A and show that the catalysts of this invention are active for the hydroformylation of 3PN.

The catalyst from 3PN hydroformylation described in the previous paragraph is isolated by filtration, washed with toluene and then suspended in another 5 mL of toluene. To this suspension is added sufficient M4P to give a 1 M solution (200 ppm Rh, 10/1 P/Rh). The reactor is then heated to 95° C. under 75 psi of CO/H$_2$. After 2 h the reactor is cooled to room temperature, vented, and the supernatant is decanted and analyzed by gas chromatography on a Quadrex-23 Capillary column. These results are summarized in Table B, which shows that upon recycle the supported catalysts of this invention remain highly active and selective for the hydroformylation of M4P.

TABLE A

Hydroformylation of 3-Pentenenitrile

| Example No. | Supported Ligand | Conversion % | Selectivity % | Linearity % | Reduction % |
|-------------|------------------|--------------|---------------|-------------|-------------|
| 62-1  | SL51 | 21.1 | 29.0 | 36.9 | 21.3 |
| 62-2  | SL52 | 25.8 | 14.6 | 20.9 | 11.2 |
| 62-3  | SL39 | 69.6 | 22.5 | 26.3 | 5.9  |
| 62-4  | SL54 | 1.0  | 29.6 | 34.0 | 13.1 |
| 62-5  | SL43 | 22.1 | 37.3 | 61.1 | 6.6  |
| 62-6  | SL44 | 22.9 | 28.1 | 46.4 | 9.2  |
| 62-7  | SL53 | 2.8  | 28.3 | 34.9 | 19.0 |
| 62-8  | SL59 | 14.5 | 17.3 | 19.7 | 12.1 |
| 62-9  | SL32 | 49.2 | 38.7 | 58.3 | 0.0  |
| 62-10 | SL36 | 26.8 | 23.3 | 53.7 | 0.0  |
| 62-11 | SL60 | 25.1 | 22.2 | 28.2 | 11.2 |
| 62-12 | SL55 | 18.1 | 21.8 | 43.8 | 8.1  |
| 62-13 | SL63 | 71.9 | 47.0 | 63.0 | 17.3 |
| 62-14 | SL62 | 59.7 | 37.8 | 49.7 | 12.4 |
| 62-15 | SL35 | 20.2 | 6.9  | 57.7 | 0.0  |
| 62-16 | SL46 | 31.6 | 35.2 | 54.0 | 5.6  |
| 62-17 | SL36 | 26.8 | 23.3 | 53.7 | 0.0  |
| 62-18 | SL58 | 8.2  | 13.3 | 47.3 | 0.0  |
| 62-19 | SL38 | 51.4 | 30.5 | 47.1 | 0.0  |
| 62-20 | SL57 | 10.1 | 44.1 | 45.9 | 3.8  |
| 62-21 | SL55 | 18.1 | 21.8 | 43.8 | 8.1  |
| 62-22 | SL77 | 11.4 | 32.8 | 42.9 | 23.5 |
| 62-23 | SL40 | 21.3 | 8.9  | 37.9 | 0.0  |
| 62-24 | SL51 | 5.6  | 9.3  | 22.4 | 0.0  |

TABLE B

Hydroformylation of Methyl 4-Pentenoate

| Example No. | Supported Ligand | Conversion % | Selectivity % | Linearity % | Reduction % |
|-------------|------------------|--------------|---------------|-------------|-------------|
| 62-25 | SL51 | 100  | 74.5  | 82.9  | 1.7 |
| 62-26 | SL52 | 99.3 | 90.6  | 92.9  | 2.1 |
| 62-27 | SL39 | 98.9 | 74.9  | 78.2  | 2.2 |
| 62-28 | SL54 | 96.1 | 90.5  | 93.7  | 3.5 |
| 62-29 | SL43 | 88.0 | 95.7  | 98.3  | 2.6 |
| 62-30 | SL44 | 74.5 | 94.6  | 97.6  | 3.0 |
| 62-31 | SL53 | 73.9 | 86.3  | 87.8  | 1.7 |
| 62-32 | SL59 | 67.5 | 95.3  | 98.0  | 2.7 |
| 62-33 | SL32 | 36.7 | 96.6  | 98.9  | 2.4 |
| 62-34 | SL36 | 19.7 | 96.4  | 100.0 | 3.6 |
| 62-35 | SL60 | 15.3 | 100.0 | 100.0 | 0   |
| 62-36 | SL55 | 15.2 | 61.7  | 61.7  | 0   |

EXAMPLE 63

Hydroformylation of Styrene

A 25 mL glass lined pressure vessel was charged with 5 mL of a solution containing 0.068 g (0.2 mmol) of Rh(CO)$_2$(acac), 6.0 wt % styrene, and 1.00 g of tetradecane (internal GC standard) in 100 mL toluene. 1.0 equiv (0.2 mmol) of polymer-supported bisphosphite was also added to the vessel. The ratio of ligand to Rh was 1 (P:Rh=2). The pressure vessel was freed from air by purging first with nitrogen (twice) and then with 1 :1 CO/H$_2$ (twice). The vessel was then pressurized to 100 psi CO/H$_2$ (1:1) and heated to 100° C. with agitation for 2 hours. The heat was shut off and the pressure vessel was allowed to cool to room temperature. The excess gases were vented and the products were analyzed by gas chromatography on a 30 M DB-Wax® capillary GC column. The results are shown in the Table below.

TABLE C

Styrene Hydroformylation with Supported Bis(phosphite)/Rhodium Catalysts

| Example No. | Supported Ligand | Conversion (%) | Linearity (%) |
|-------------|------------------|----------------|---------------|
| 63-1 | SL70 | 100 | 84 |
| 63-2 | SL71 | 100 | 85 |
| 63-3 | SL72 | 100 | 73 |
| 63-4 | SL67 | 100 | 75 |
| 63-5 | SL66 | 50  | 69 |

Although particular embodiments of the present invention have been described in the foregoing description, it will be understood by those skilled in the art that the invention is capable of numerous modifications, substitutions and rearrangements without departing from the spirit or essential attributes of the invention. Reference should be made to the appended claims, rather than to the foregoing specification, as indicating the scope of the invention.

What is claimed is:

1. A process for the preparation of a supported rhodium bisphosphite hydroformylation catalyst comprising reacting CO and $H_2$ with a rhodium compound in the presence of a supported bis(phosphorus) ligand of formula 1

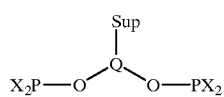

1 in which Q is any organic fragment which binds the two phosphorus moieties to the support and X is alkoxy, aryloxy, alkyl, or aryl, or alternatively wherein the $PX_2$ moiety forms a ring and $X_2$ is a di(alkoxy), di(aryloxy), di(alkyl), or di(aryl).

2. A process according to claim 1 where the supported ligand of Formula (1) is further characterized according to Formula (4)

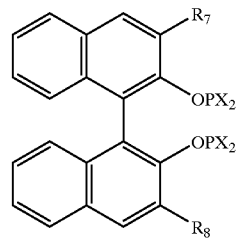

4 wherein:

the linker Q is a 2,2'-dihydroxyl-1,1'-binaphthalene bridging group;

the substituents $R_7$ and $R_8$ in the 3,3' positions of the binaphthalene bridging group are selected from alkyl group containing 2 to 10 carbon atoms, an aryl group, an alkoxy group, an aryloxy group, a carboalkoxy group, a carboaryloxy group, a nitrile group, a triarylsilyl group, or trialkylsilyl group;

at least one of the groups $R_7$ and $R_8$ are covalently attached to a support (Sup);

X is an alkoxy, aryloxy, alkyl, or aryl, or alternatively the $PX_2$ moiety forms a ring and $X_2$ is a di(alkoxy), di(aryloxy), di(alkyl), or di(aryl).

3. A process according to claim 1 wherein the temperature is in the range 25–120° C. and CO and $H_2$ partial pressures in the range 0.1–3.4 MPa.

4. A process according to claim 3 wherein the rhodium compound is dissolves in a solvent which is a good swelling solvent for the support.

5. A process according to claim 1 wherein the support is an organic polymer resin.

6. A process according to claim 1 wherein the organic polymer resin is a crosslinked polystyrene resin.

7. A hydroformylation catalyst composition according to claim 2, characterized in that $R^7$ and $R^8$ are carboalkoxyl groups, CO—O—R, in which R is a $C_1$–$C_{20}$ alkyl or a $C_6$–$C_{20}$ aryl.

* * * * *